US011446429B2

(12) United States Patent
Pratt et al.

(10) Patent No.: US 11,446,429 B2
(45) Date of Patent: Sep. 20, 2022

(54) SYSTEMS AND METHODS FOR MANAGING PNEUMATIC PATHWAYS IN INTEGRATED MULTILAYER WOUND DRESSINGS

(71) Applicant: KCI Licensing, Inc., San Antonio, TX (US)

(72) Inventors: Benjamin A. Pratt, Wimborne (GB); Colin John Hall, Wimborne (GB); Thomas Edwards, Wimborne (GB); David Richard Mercer, San Antonio, TX (US); James Seddon, Wimborne (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 17/056,536

(22) PCT Filed: May 16, 2019

(86) PCT No.: PCT/US2019/032617
§ 371 (c)(1),
(2) Date: Nov. 18, 2020

(87) PCT Pub. No.: WO2019/226454
PCT Pub. Date: Nov. 28, 2019

(65) Prior Publication Data
US 2021/0205527 A1 Jul. 8, 2021

Related U.S. Application Data

(60) Provisional application No. 62/674,970, filed on May 22, 2018.

(51) Int. Cl.
*A61M 1/00* (2006.01)
*A61F 13/00* (2006.01)
*A61M 3/02* (2006.01)

(52) U.S. Cl.
CPC ..... *A61M 3/0283* (2013.01); *A61F 13/00068* (2013.01); *A61M 1/85* (2021.05);
(Continued)

(58) Field of Classification Search
CPC ........ A61M 3/0283; A61M 1/85; A61M 1/90; A61M 3/0254; A61M 2210/1021; A61F 13/00068; A61F 13/0216
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Tatyana Zalukaeva
*Assistant Examiner* — Nhu Q. Tran

(57) ABSTRACT

A system for providing instillation fluid to a deep abdominal wound includes an instillation module and a connection structure. The instillation module defines a first surface and a second, abdominal contents-facing surface. The instillation module includes a distribution hub configured to receive instillation fluid from an instillation fluid source. The connection structure includes a first surface, a second, abdominal contents-facing surface; and a flow path extending
(Continued)

between the first surface and the second surface. The flow path includes an inlet configured to receive an instillation fluid conduit engaged with the instillation fluid source and an outlet in fluid communication with the instillation module. The flow path defines an axis extending between the inlet and the outlet. The flow path is configured to compress in a direction defined by the axis.

9 Claims, 15 Drawing Sheets

(52) U.S. Cl.
CPC ............ *A61M 1/90* (2021.05); *A61M 3/0254* (2013.01); *A61M 2210/1021* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,084,064 A * | 1/1992 | Barak .................. A61M 60/859 623/1.31 |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0016815 A1 * | 1/2010 | Vitaris ................ A61F 13/0226 604/304 |
| 2011/0257572 A1 | 10/2011 | Locke et al. |
| 2012/0101458 A1 | 4/2012 | Hall et al. |
| 2012/0136326 A1 * | 5/2012 | Croizat ............ A61F 13/00017 604/319 |
| 2013/0066286 A1 | 3/2013 | Croizat et al. |
| 2014/0276489 A1 * | 9/2014 | Robinson ................ A61M 1/73 604/319 |
| 2015/0165182 A1 * | 6/2015 | Pratt ..................... A61M 37/00 604/290 |
| 2017/0209641 A1 | 7/2017 | Mercer et al. |
| 2018/0042521 A1 * | 2/2018 | Ryu .................... A61B 5/1073 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3 257 438 A1 | 12/2017 |
| GB | 692578 A | 6/1953 |
| GB | 2 195 255 A | 4/1988 |
| GB | 2 197 789 A | 6/1988 |

(56) References Cited

FOREIGN PATENT DOCUMENTS

| | | | |
|---|---|---|---|
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2016015001 A2 * | 1/2016 | .......... A61M 3/0254 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion in International Application No. PCT/US2019/032617, dated Oct. 2, 2019.

* cited by examiner

SYSTEMS AND METHODS FOR MANAGING PNEUMATIC PATHWAYS IN INTEGRATED MULTILAYER WOUND DRESSINGS

CROSS-REFERENCE TO RELATED APPLICATIONS

This Application claims the benefit of priority to international patent application number PCT/US2019/032617, filed on May 16, 2019, which claims the benefit of priority to U.S. Provisional Application No. 62/674,970, filed on May 22, 2018, the complete disclosures of which are hereby incorporated herein by reference in their entireties.

BACKGROUND

The present disclosure relates generally to a wound therapy system, and more particularly to a wound therapy system configured to provide instillation therapy and negative pressure wound therapy to a fascial incision in a deep abdominal incision.

Instillation therapy is a type of wound therapy that involves applying a therapeutic fluid (e.g. a saline solution, a prescribed solution, an antibiotic, a cleaning fluid etc.) to a treatment site to promote wound healing and granulation, prevent the wound from drying out, prevent the wound from becoming infected by bacteria and/or treat an infected treatment site. Some instillation systems include an instillation fluid container and an instillation pump for providing instillation fluid to the treatment site. Instillation therapy can be used in conjunction with NPWT or can be used separately.

Negative pressure wound therapy (NPWT) is a type of wound therapy that involves applying negative pressure (pressure lower than atmospheric pressure) to a treatment site to promote wound healing. NPWT applies negative pressure to the wound to drain fluids from the wound as the wound heals. Some NPWT systems include a pump which operates to maintain the treatment site at negative pressure by removing wound exudate from the treatment site. The wound exudate is typically routed to a canister or other container fluidly connected to the pump where the wound exudate is stored until emptied by a user.

Both instillation therapy and NPWT can be used to treat deep abdominal wounds due to abdominal laparotomies, which are used to gain access to the abdominal cavity for surgery and/or to relieve intra-abdominal pressure by allowing the bowels to expand. In some instances, the laparotomy incision is not immediately closed, resulting in an "open abdomen," and instillation and/or NPWT may be used to treat the open abdomen. For example, instillation fluid can be used to irrigate the open abdomen, preventing the abdominal contents from drying out and can also be used to periodically wash out the open abdomen to potentially reduce a likelihood of sepsis. However, manual washouts can result in damage that requires further surgery.

Instillation and negative pressure systems adapted to treat the open abdomen are often complicated because of the need to maintain fluidly separated instillation and NWPT pathways, and the fluidly separate instillation and NPWT pathways may be difficult to identify in wound treatment systems that are deployed in a patient. Furthermore, the wound therapy system may expand and contract during cycles of instillation and NPWT, making it difficult to maintain fluid-tight seals on the instillation pathway and the NPWT pathway. Furthermore, hard instillation and/or NPWT connectors may contact the patient or otherwise cause patient discomfort during connection of the instillation and/or NPWT connectors or during the compression that occurs during NPWT.

SUMMARY

One implementation of the present disclosure is a system for providing instillation fluid to a deep abdominal wound includes an instillation module and a connection structure. The instillation module defines a first surface and a second, abdominal contents-facing surface. The instillation module includes a distribution hub configured to receive instillation fluid from an instillation fluid source. The connection structure includes a first surface, a second, abdominal contents-facing surface; and a flow path extending between the first surface and the second surface. The flow path includes an inlet configured to receive an instillation fluid conduit engaged with the instillation fluid source and an outlet in fluid communication with the instillation module. The flow path defines an axis extending between the inlet and the outlet. The flow path is configured to compress in a direction defined by the axis.

Another implementation of the present disclosure is a connection structure for providing instillation fluid to a deep abdominal wound. The connection structure includes a first surface, a second, abdominal contents-facing surface, and a flow path extending between the first surface and the second surface. The flow path includes an inlet configured to receive an instillation fluid conduit engaged with an instillation fluid source and an outlet configured for fluid communication with an instillation module positionable within the deep abdominal wound. The flow path defines an axis extending between the inlet and the outlet. The flow path is configured to compress in a direction defined by the axis.

Another implementation of the present disclosure is a system for providing instillation fluid to a deep abdominal wound. The system includes a sealing member and a wound dressing. The sealing member defines a first surface and a second, abdominal contents-facing surface. The sealing member is configured to form a fluid-tight seal about a perimeter of the deep abdominal wound. The wound dressing includes an instillation module, an instillation conduit, and a sealing plate. The instillation module defines a first surface and a second, abdominal contents-facing surface. The instillation module includes a distribution hub portion configured to receive instillation fluid from an instillation fluid source. The instillation conduit includes a first end in fluid communication with the instillation module and a second end configured for fluid communication with an instillation fluid source. The sealing plate includes an instillation conduit passage extending from the instillation fluid plate. The sealing plate is configured to receive the instillation conduit therethrough. The sealing plate is securable to the first surface of the sealing member.

Another implementation of the present disclosure is a connection system for providing instillation therapy and negative pressure therapy to a deep abdominal wound. The connection system includes an instillation module, a negative pressure manifold, and a connection plate. The instillation module defines a first surface and a second, abdominal contents-facing surface. The instillation module includes a distribution hub portion including an instillation inlet configured to engage an instillation conduit of an instillation fluid source. The negative pressure manifold includes a first surface and a second, abdominal contents-facing surface. The connection plate is secured to the negative pressure manifold and includes an instillation inlet connector having a first shape in fluid communication with the installation inlet of the installation module and a negative pressure inlet connector having a second shape different than the first shape. The negative pressure inlet connector is in fluid communication with the negative pressure manifold.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
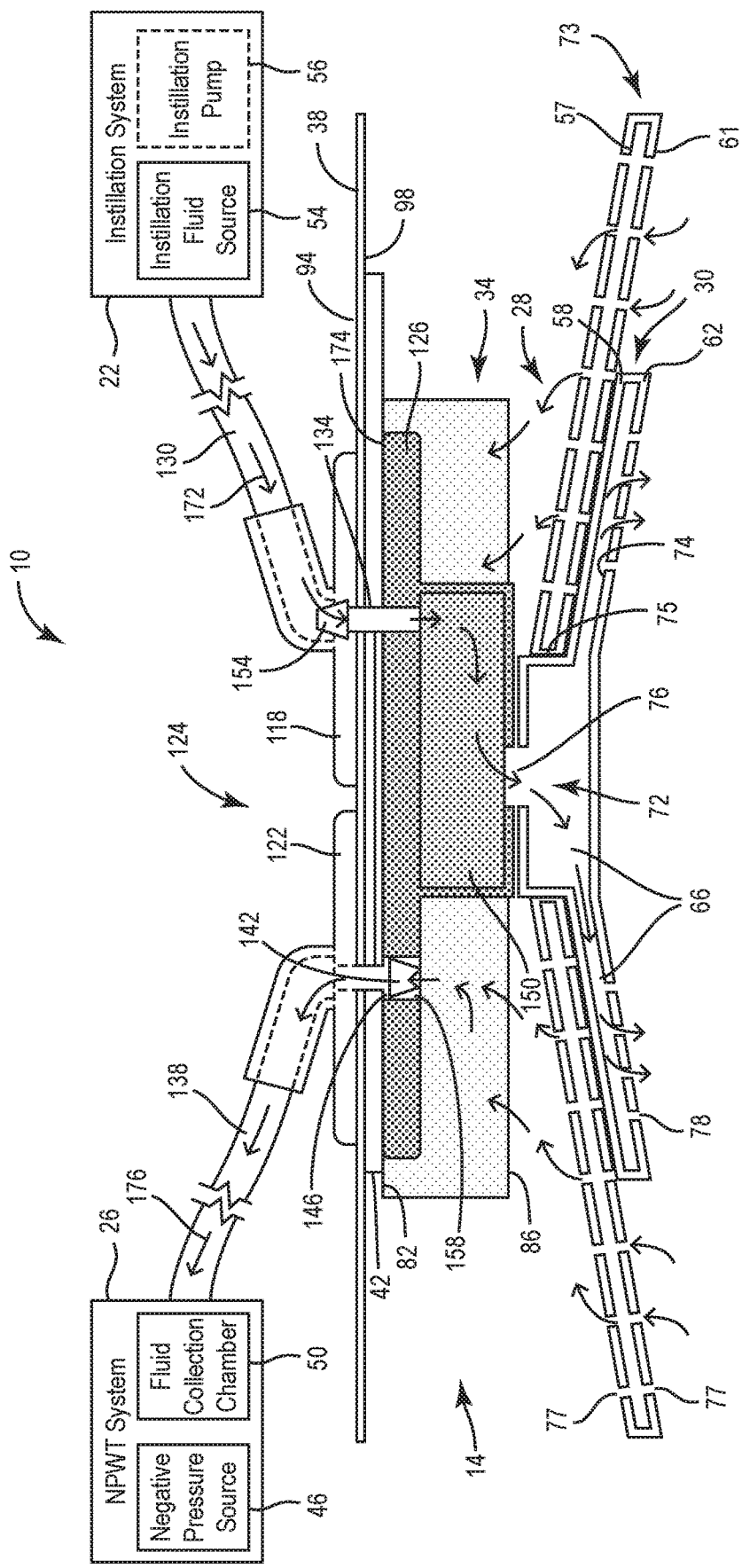
FIG. 1 is a section view of wound treatment system according to some embodiments.

Referring generally to the FIGURES, a wound therapy system with installation and negative pressure wound therapy (NPWT) systems and components thereof are shown, according to various exemplary embodiments. The wound therapy system may include a wound dressing, an installation system, and a NPWT system. The wound therapy system may include an installation module for delivering installation fluid to a treatment site, a negative pressure manifold for providing NPWT to the treatment site, a connection plate for facilitating connection of the installation system and/or NPWT system components to the wound dressing, and a sealing member for forming a substantially fluid-tight seal around the treatment site. The wound therapy system is configured to include an installation flow path that is fluidly separate from the NPWT flow path. The installation system may include an installation fluid source and an installation pump. The NPWT system may include a negative pressure source and a fluid collection container. The phrase "negative pressure" means a pressure less than an ambient or atmospheric pressure.

In some embodiments, the connection plate is configured to facilitate connecting the installation system components to the wound dressing system and connecting the NPWT system components to the wound dressing system. For example, the connection plate may include an installation inlet having a first shape and a NPWT inlet having a second shape different than the first shape. The installation system may include an installation conduit pad configured to engage the installation inlet but the NPWT inlet. The NPWT system may include a NPWT conduit pad configured to engage the NPWT inlet but not the installation inlet.

In some embodiments, the negative pressure manifold is configured to include an installation flow path in fluid communication with the installation module. The installation flow path is fluidly separate from the negative pressure manifold such that the installation fluid flowing along the installation flow path does not flow into the negative pressure manifold. In some embodiments, the installation flow path is configured to expand and compress with the negative pressure manifold during cycles of NPWT. In some embodiments, the installation flow path may be a bellows structure made of an installation-fluid impermeable material that is positioned within a through-hole in the negative pressure manifold. The bellows structure may be configured to extend or retract to accommodate different thicknesses and/or materials of negative pressure manifold. In some embodiments, the installation flow path is made of the same material as the negative pressure manifold such that the installation flow path has substantially the same compression and expansion as the negative pressure manifold during cycles of NPWT. In such embodiments, an first surface, a second, abdominal contents-facing surface, and a flow path (e.g., channel) formed within the installation flow path are coated with an installation fluid-impermeable material. The first surface is secured to the connection plate or the sealing member in a fluid-tight connection and the second surface is secured to the installation module proximate an inlet of the installation module in a fluid-tight connection to generate an installation flow path that is fluidly separate from the NPWT flow path.

In some embodiments, the installation module includes an integrated installation conduit. The integrated installation conduit may wrap around a side of the negative pressure manifold to abut the sealing member and/or pass through the negative pressure manifold.

The integrated installation conduit can be made of a tubing material that is impermeable to installation fluid or can be positioned within an envelope that is impermeable to installation fluid.

In some embodiments, the installation module may include an integrated installation conduit that is engaged with a sealing system for forming a substantially fluid-tight seal about a hole in the sealing member that receives the integrated installation conduit. To deploy the installation module and sealing system, the instillation module may be positioned in the treatment site such that the instillation module substantially overlies the abdominal contents. The instillation conduit is then passed around or through the negative pressure manifold and then through the hole in the sealing member. A sealing plate having an instillation conduit passageway is then slid along the instillation conduit until the sealing plate abuts the sealing member. The sealing plate is then secured to the sealing member using an adhesive. A locking collar is friction-fit about an exterior surface of the installation conduit passageway to form a substantially fluid-tight seal between the instillation conduit passageway and the instillation conduit.

Additional features and advantages of the wound therapy system are described in detail below.

Wound Therapy System

Referring to FIG. 1, a section view of a wound therapy system 10 is shown, according to an exemplary embodiment. In the illustrated embodiment, the wound therapy system is configured to treat the abdominal cavity and is discussed in the context of treating an open abdomen. The wound therapy system 10 can be used to treat an "open abdomen" condition, in which a deep abdominal wound is left open for a period of time. The components described herein may be used in different configurations of instillation therapy systems and/or negative pressure wound therapy (NPWT) systems. The phrase "negative pressure" means a pressure less than an ambient or atmospheric pressure.

Figure 5:
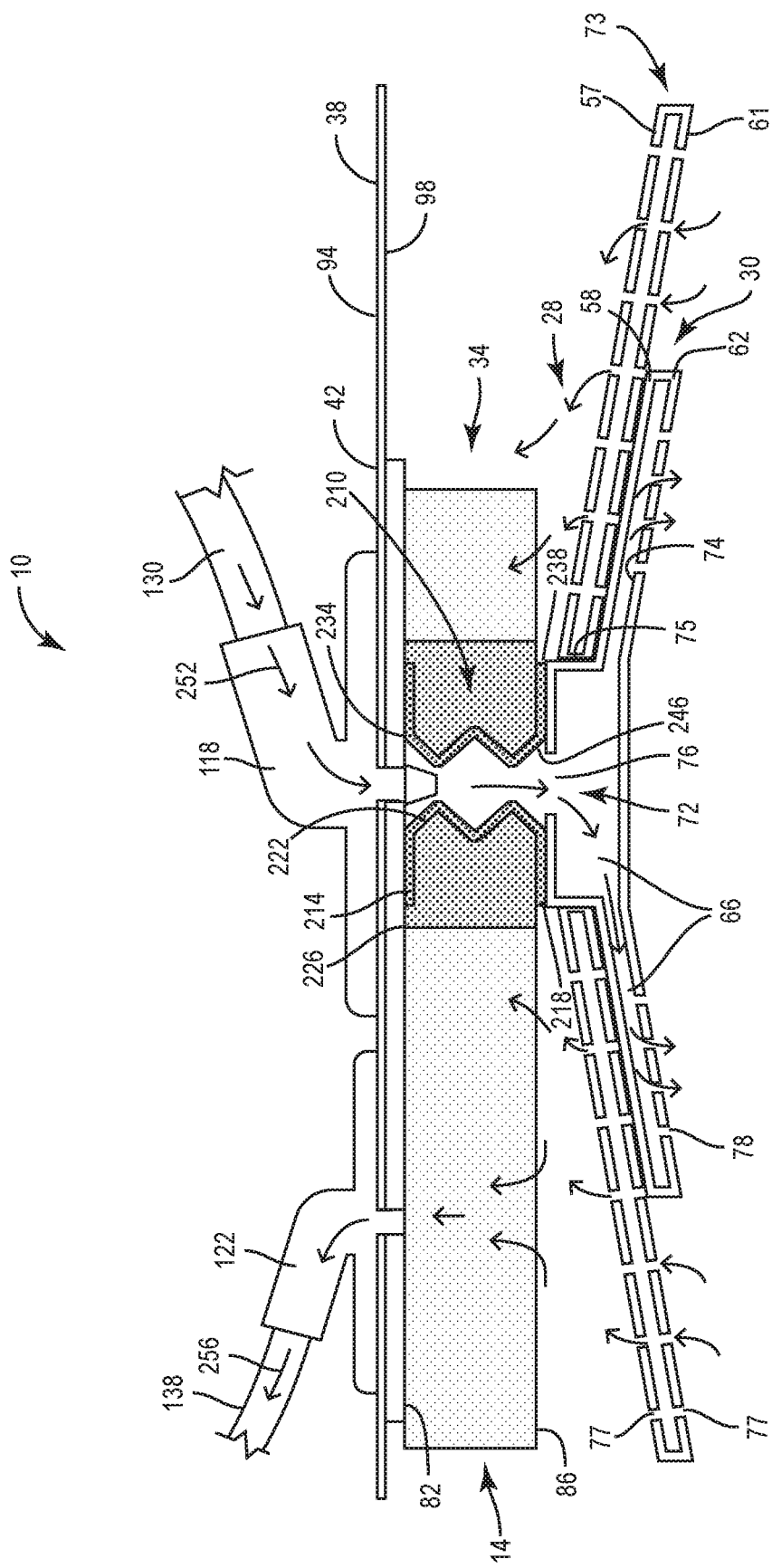
FIG. 5 is a section view of a wound treatment system including the installation fluid conduit of FIG. 4 according to some embodiments.

In various embodiments, the wound therapy system 10 can be used to treat a deep abdominal incision. The wound therapy system 10 includes a wound dressing 14, an instillation system 22, and a NPWT system 26. The wound dressing 14 includes an abdominal treatment device 28, an instillation module 30, a negative pressure manifold 34, a sealing member 38, and an optional connection plate 42 (FIG. 5). The wound dressing 14 is intended for engagement with a treatment site of a patient, such as an abdominal cavity of a patient. The wound therapy system 10 can be used with the NPWT system 26 and/or the instillation system 22. The NPWT system 26 may include a negative pressure source 46, such as a pump, and a fluid collection chamber 50. The instillation system 22 may include an instillation fluid source 54. In some embodiments, the instillation system 22 may include an installation pump 56.

The Abdominal Treatment Device

Figure 12:
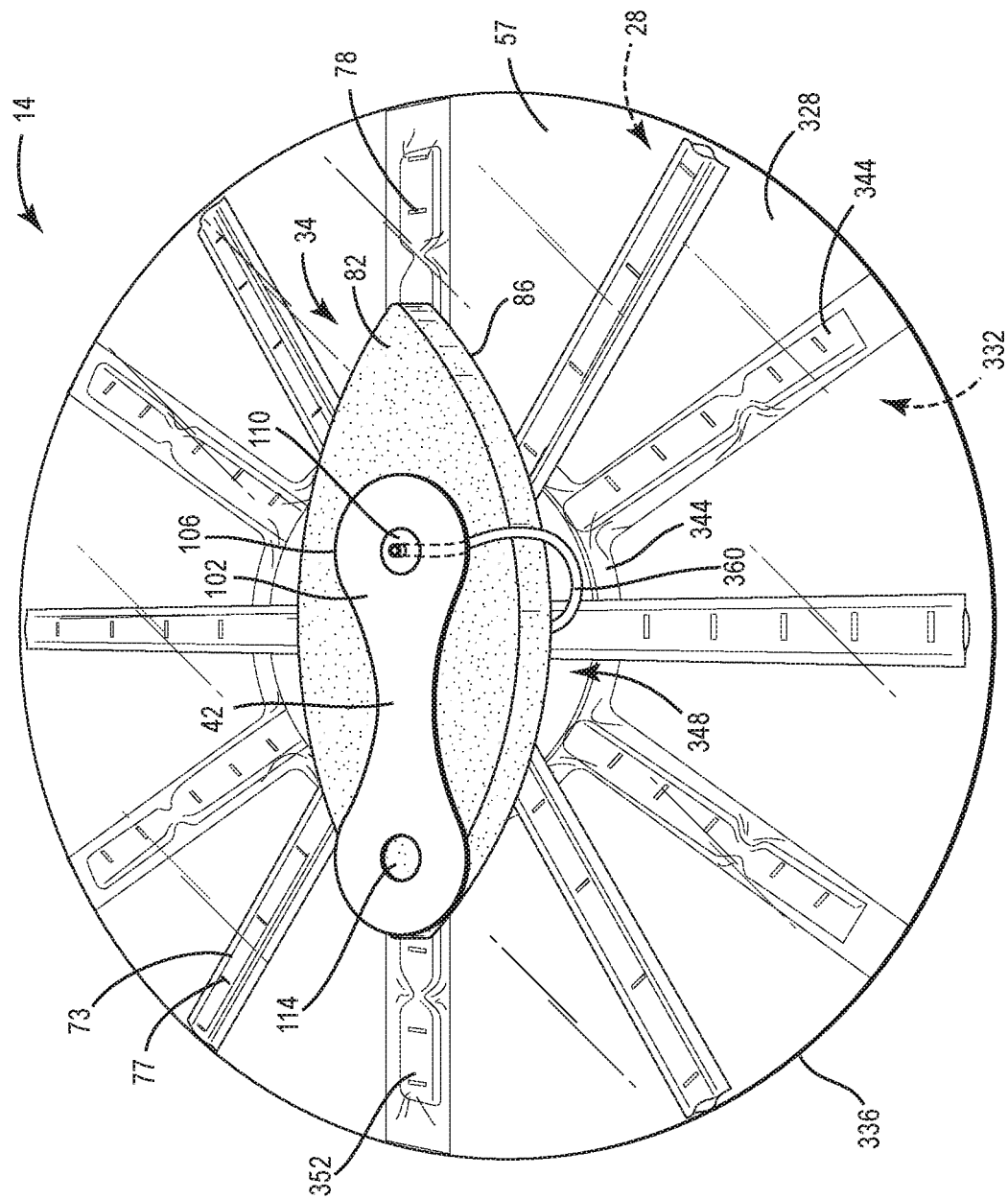
FIG. 12 is a perspective view of a wound treatment system including the installation module of FIG. 11 according to some embodiments.

Referring to FIG. 1, the abdominal treatment device 28 is shown to include a first layer 57, a second layer 61, and a foam spacer 65. The second layer 61 faces the abdominal contents and is generally opposite the first layer 57. The foam spacer 65 includes a first surface 67 and a second, abdominal contents-facing surface 69. The foam spacer 65 includes a hub 71 and a plurality of leg members 73 that extend generally radially from the hub 71. The hub 71 includes a through-opening 75 for receiving at least portion of the instillation module 30. The foam spacer 65 is generally in fluid communication with a negative pressure conduit 138 to receive negative pressure from the negative pressure source 46 and to receive fluids flowing from the treatment site towards the negative pressure source 46. The plurality of elongate legs 73 are configured to distribute negative pressure throughout the treatment site. As illustrated in FIG. 12, the first layer 57 and the second layer 61 encapsulate the leg members 73, the hub 71, and the intervening space between adjacent leg members 73. In the illustrated embodiment, the hub 71 and the plurality of leg members 73 are made of a material that is substantially hydrophobic and structured for fluid flow under substantially atmospheric pressure conditions and under negative pressure conditions. In some embodiments, the hub 71 and the plurality of leg members 73 are made of a reticulated foam, such as the reticulated foam described below with respect to the negative pressure manifold 34. In some embodiments, the leg members 73 may be cut to accommodate relatively small wounds. The first layer 57 and the second layer 61 of the abdominal treatment device 28 can made of a material that is fluid-impermeable and intended to not irritate the patient's fascia and internal organs. The abdominal treatment device 28 may include a plurality of fenestrations 77 (e.g., negative pressure inlets) for distribution of negative pressure by the plurality of leg members 73 and/or to permit fluid to flow into the plurality of leg members 73 and/or the space between the plurality of leg members 73 and the layers 57, 61. The fenestrations 77 may include through-holes, slits, or linear cuts. The fenestrations 77 may be circular, rectangular, polygonal, or be any other shape in cross-section.

The Instillation Module

Referring to FIG. 1, the instillation module 30 is shown to include a first layer 58, a second layer 62, and a fluid distribution layer 66. The second layer 62 faces the abdominal contents and is generally opposite the first layer 58. The fluid distribution layer 66 includes a first surface 68 and a second, abdominal contents-facing surface 70. The fluid distribution layer 66 includes a fluid distribution hub 72 and a plurality of fluid distribution structures 74 that extend generally radially from the fluid distribution hub 72. The fluid distribution hub 72 is generally in fluid communication with an instillation conduit 130 to receive instillation fluid and in fluid communication with the fluid distribution structures to distribute instillation fluid to the fluid distribution structures 74. For example, the first layer 58 may include an opening 76 (e.g., an instillation inlet) proximate the fluid distribution hub 72 for providing fluid communication between the fluid distribution hub 72 and the instillation connection structure. The first layer 58 and the second layer 62 are welded together along at least a portion of the edges of the first layer 58 and the second layer 62 to encapsulate the fluid distribution layer 66. In some embodiments, the first layer 58 and the second layer 62 encapsulate the fluid distribution structures 74 and the fluid distribution hub 72, but not the intervening space between adjacent fluid distribution structures 74 (FIG. 5). In the illustrated embodiment, the fluid distribution hub 72 and the plurality of fluid distribution structures 74 are made of a material that is substantially hydrophobic and structured for fluid flow under substantially atmospheric pressure conditions and under negative pressure conditions. In some embodiments, the fluid distribution hub 72 and the plurality of fluid distribution structures 74 are made of a reticulated foam, such as the reticulate foam described below with respect to the negative pressure manifold 34. In some embodiments, the fluid distribution structures 74 may be cut to accommodate relatively small wounds.

In other embodiments, the first layer 58 and the second layer 62 can be made of a material that is fluid-impermeable and intended to not irritate the patient's fascia and internal organs. As described in greater detail below, in such an embodiment, first layer 58 and the second layer may fluid distribution layer and include a plurality of fenestrations 78 (e.g., instillation outlets) for distribution of instillation fluid by the plurality of fluid distribution structures 74. The fenestrations 78 may include through-holes, slits, or linear cuts. The fenestrations 78 may be circular rectangular, polygonal, or be any other shape in cross-section.

The Negative Pressure Manifold

Figure 2:
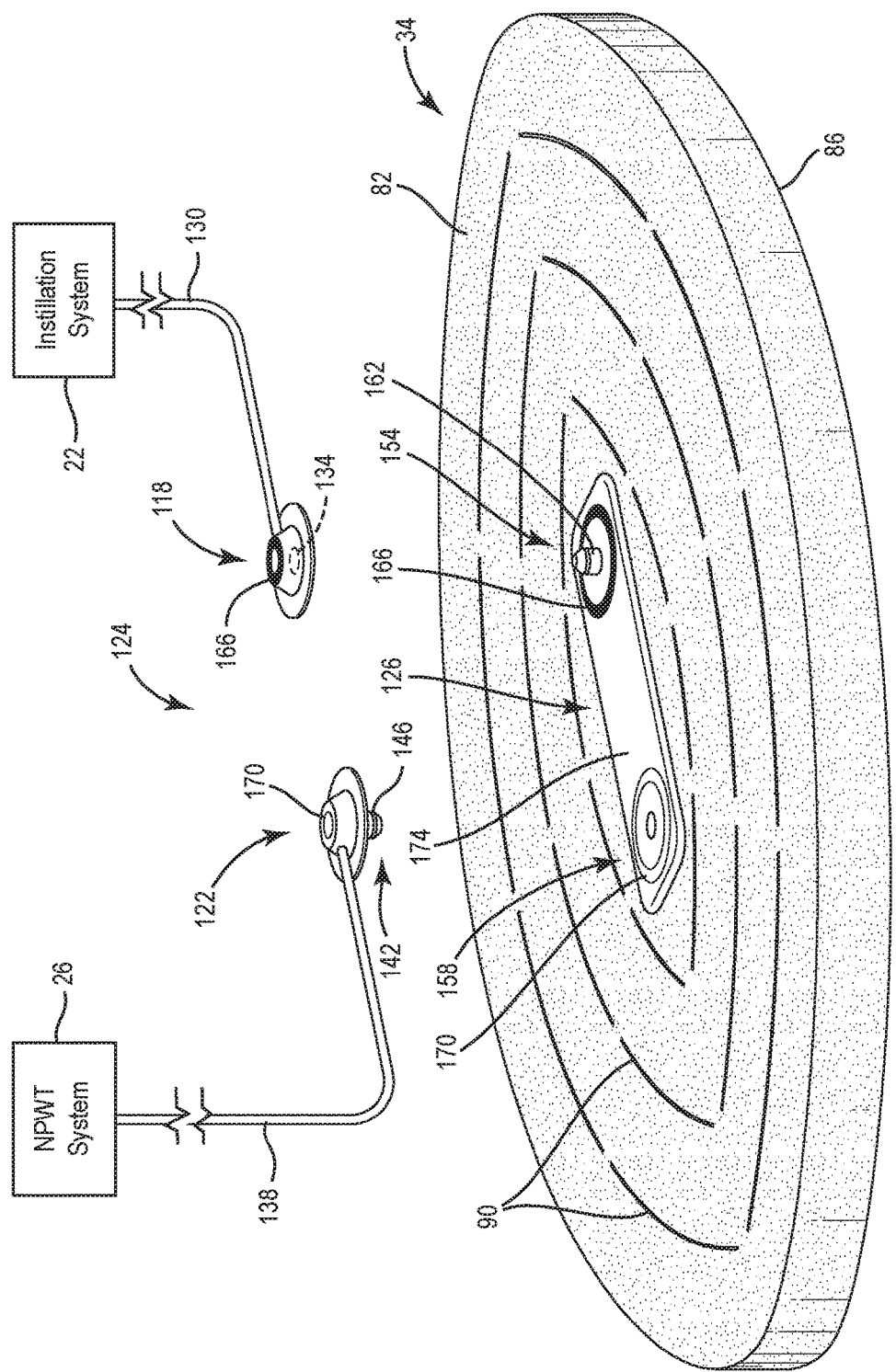
FIG. 2 is a perspective view of a connection system for use with the wound treatment system of FIG. 1 according to some embodiments.

Referring to FIGS. 1-2, the negative pressure manifold 34 is shown to include a first surface 82 and a second, abdominal contents-facing surface 86 opposite the first surface 82. When the negative pressure manifold 34 is applied to the treatment site, the first surface 82 faces away from the abdominal contents, whereas the second surface 86 faces toward the abdominal contents. In some embodiments, the first surface 82 of the negative pressure manifold 34 contacts the second surface 86 of the sealing member 38. In some embodiments, the negative pressure manifold 34 may include perforations 90 to facilitate removal of a portion of the negative pressure manifold 34 to accommodate different sizes of wounds. In some embodiments, the second surface 86 of the negative pressure manifold 34 contacts the instillation module 30. The negative pressure manifold 34 is adapted to wick fluid (e.g. exudate) from the wound and includes in-molded manifold structures for distributing negative pressure throughout the negative pressure manifold 34 during negative pressure wound therapy treatments. The negative pressure manifold 34 is made from a material that allows fluid and/or negative pressure to pass from between at least a first portion of the negative pressure manifold 34 and a second portion of the negative pressure manifold 34. In some embodiments, the negative pressure manifold 34 may include in-molded flow channels or pathways that can distribute the fluids provided to and removed around the manifold. In some embodiments, the in-molded flow channels or pathways can be formed by the cells in a porous foam material.

The negative pressure manifold 34 can be made from a porous and permeable foam-like material and, more particularly, a reticulated, open-cell polyurethane or polyether foam that allows good permeability of wound fluids while under a reduced pressure. One such foam material that has been used is the VAC® Granufoam® material that is available from Kinetic Concepts, Inc. (KCI) of San Antonio, Tex. Any material or combination of materials might be used for the negative pressure manifold 34 provided that the negative pressure manifold 34 is operable to distribute the reduced pressure and provide a distributed compressive force along the treatment site.

The reticulated pores of the Granufoam® material that are in the range from about 400 to 600 microns, are preferred, but other materials may be used. The density of the absorbent layer material, e.g., Granufoam® material, is typically in the range of about 1.3 lb/ft$^3$-1.6 lb/ft$^3$ (20.8 kg/m$^3$-25.6 kg/m$^3$). A material with a higher density (smaller pore size) than Granufoam® material may be desirable in some situations. For example, the Granufoam® material or similar material with a density greater than 1.6 lb/ft$^3$ (25.6 kg/m$^3$) may be used. As another example, the Granufoam® material or similar material with a density greater than 2.0 lb/ft$^3$ (32 kg/m$^3$) or 5.0 lb/ft$^3$ (80.1 kg/m$^3$) or even more may be used. The more dense the material is, the higher compressive force that may be generated for a given reduced pressure. If a foam with a density less than the tissue at the tissue site is used as the absorbent layer material, a lifting force may be developed. In one illustrative embodiment, a portion, e.g., the edges, of the wound dressing may exert a compressive force while another portion, e.g., a central portion, may provide a lifting force.

The absorbent layer material may be a reticulated foam that is later felted to thickness of about one third (⅓) of the foam's original thickness. Among the many possible absorbent layer materials, the following may be used: Granufoam® material or a Foamex® technical foam (www.foamex.com). In some instances, it may be desirable to add ionic silver to the foam in a microbonding process or to add other substances to the absorbent layer material such as antimicrobial agents. The absorbent layer material may be isotropic or anisotropic depending on the exact orientation of the compressive forces that are desired during the application of reduced pressure. The absorbent layer material may also be a bio-absorbable material.

The Sealing Member

Referring again to FIG. 1, the sealing member 38 is shown to include a first surface 94 and a second, wound-facing, surface 98 opposite the first surface 94. When the wound therapy system 10 is applied to a wound, the first surface 94 faces away from the wound, whereas the second surface 98 faces toward the wound. As is shown in FIG. 1, at least a perimeter of the second surface 98 includes an adhesive. The adhesive is intended to secure sealing member 38 to the patient's skin and to form a fluid-tight seal about the incision. The sealing member 38 also provides a barrier to passage of microorganisms through the wound therapy system 10.

In some embodiments, the sealing member 38 is an elastomeric material or may be any material that provides a fluid seal. "Fluid seal" means a seal adequate to hold pressure at a desired site given the particular reduced-pressure subsystem involved. The term "elastomeric" means having the properties of an elastomer and generally refers to a polymeric material that has rubber-like properties. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, thermoplastic polyurethane (TPU), and silicones. As non-limiting examples, the sealing member 38 may be formed from materials that include a silicone, 3M Tegaderm® drape material, acrylic drape material such as one available from Avery, or an incise drape material. In some embodiments, the sealing member 38 may be at least partially transparent to facilitate viewing of the wound therapy system 10 through the sealing member 38 as described in greater detail below.

The sealing member 38 may be substantially impermeable to liquid and substantially permeable to water vapor. In other words, the sealing member 38 may be permeable to water vapor, but not permeable to liquid water or wound exudate. This increases the total fluid handling capacity (TFHC) of wound therapy system 10 while promoting a moist wound environment. In some embodiments, the sealing member 38 is also impermeable to bacteria and other microorganisms. In some embodiments, the sealing member 38 is configured to wick moisture from the negative pressure manifold 34 and distribute the moisture across the first surface 94. In some embodiments, the adhesive applied to the second surface 98 of the sealing member 38 is moisture vapor transmitting and/or patterned to allow passage of water vapor therethrough.

The Connection Plate

Figure 6:
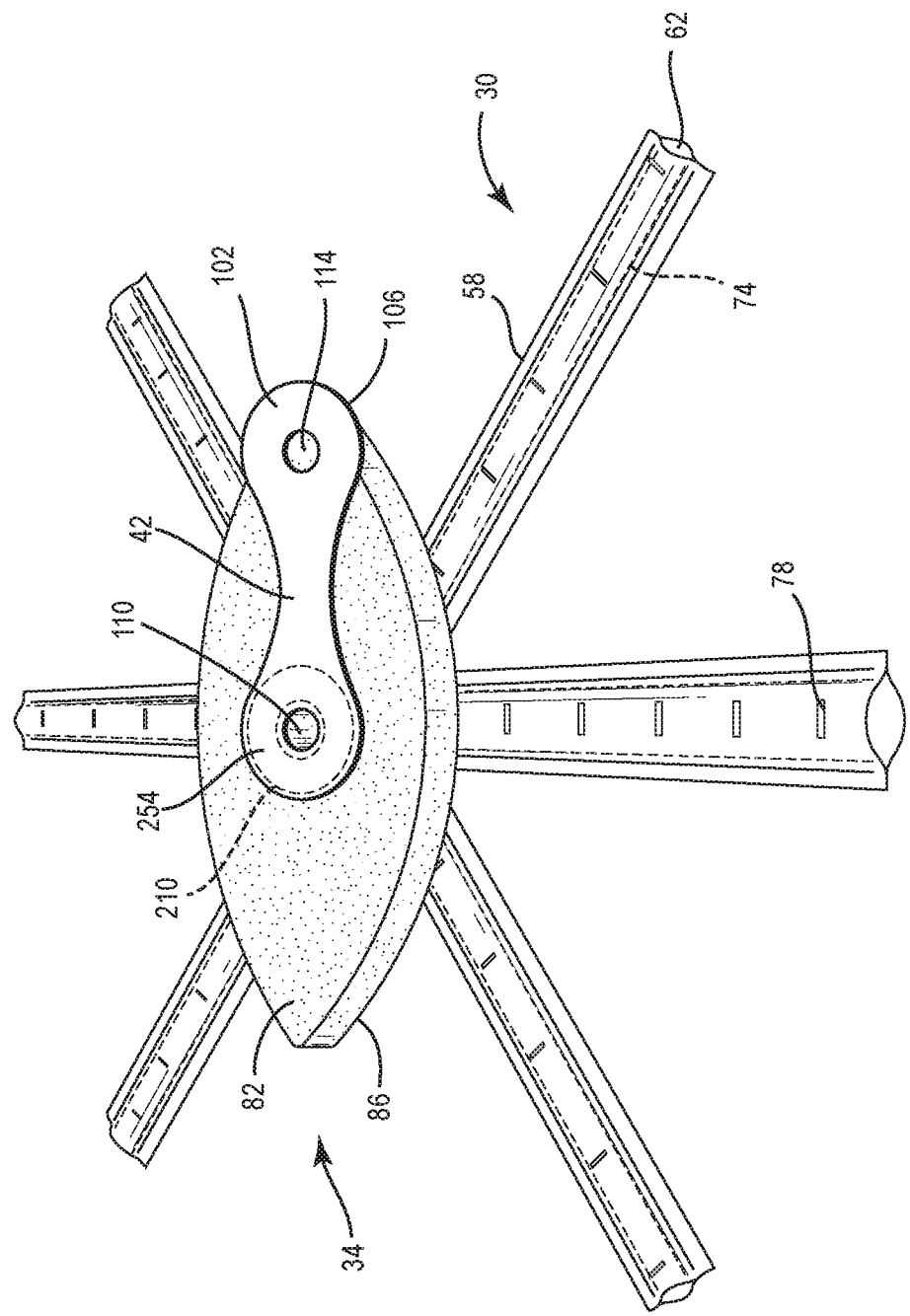
FIG. 6 is a perspective view of a wound treatment system including the installation fluid conduit of FIG. 4 according to some embodiments.

Referring now to FIG. 6, the connection plate 42 includes first surface 102 and a second, abdominal contents-facing surface 106. The connection plate 42 includes an instillation inlet 110 and a NPWT inlet 114. In the illustrated embodiment, the connection plate 42 is a relatively dense material that functions as a land for the instillation conduit pad 118 and the NPWT conduit pad 122. The connection plate 42 also provides a visual indication of where to cut or pierce the sealing member 38 when connecting the instillation conduit pad 118 and the NPWT conduit pad. For example, the connection plate 42 may include markings (e.g., colors, patterns, words, etc.) to assist an operator in positioning the installation conduit pad 118 and the NPWT conduit pad 122. For example, in the illustrated embodiment, visual contrast between a color of the connection plate 42 and a color of the negative pressure manifold 34 may assist the operator in correctly positioning the installation conduit pad 118 and the NPWT conduit pad 122. In some embodiments, the connection plate 42 may include an adhesive layer on the second surface 106 of the connection plate 42 for securing the connection plate 42 to the negative pressure manifold 34 to prevent the connection plate 42 from slipping.

Installation and NPWT Conduit Connection System-Separate Installation and NPWT Pads Referring now to FIGS. 1-2, a connection system 124 for the connecting the wound therapy dressing to the installation system 22 and the NPWT system 26 is shown according to some embodiments. FIG. 1 illustrates a section view of the connection system 124 mounted on the negative pressure manifold 34. FIG. 2 illustrates a perspective view of the connection system 124 engaged with the wound dressing 14.

The connection system 124 is shown to include a connection plate 126, an installation conduit pad 118, and a NPWT conduit pad 122. The installation conduit pad 118 is secured to an installation conduit 130 of the installation system 22 through a substantially fluid-tight connection. The installation conduit pad 118 includes an installation outlet connector 134 configured to engage the connection plate 126 as described in greater detail below. In the illustrated embodiment, the installation outlet connector 134 is a hole. The NPWT conduit pad 122 is secured to a negative pressure conduit 138 of the NPWT system 26 through a substantially fluid-tight connection. The NPWT conduit pad 122 includes an NPWT outlet connector 142 configured to engage the connection plate 126 as described in greater detail below. In the illustrated embodiment, the NPWT outlet connector 142 is a protrusion. In some embodiments, the NPWT outlet connector 142 is a pointed protrusion (e.g., spear). In some embodiments, the NPET outlet connector includes a barb 146. As shown in FIG. 1, in some embodiments, the installation conduit 130 and the negative pressure conduit 138 are made of low-profile and/or flexible tubing to reduce patient discomfort.

The connection plate 126 is secured to the first surface 82 of the negative pressure manifold 34. The connection plate 126 includes an installation connection structure 150 (FIG. 1), an installation inlet connector 154, and a NPWT inlet connector 158. The installation connection structure 150 extends through the negative pressure manifold 34 (e.g., between the first surface 82 and the second surface 86) to facilitate fluid communication between the installation inlet connector 154 and the fluid distribution hub 72. The installation connection structure 150 is configured to prevent lateral flow of the installation fluid into the negative pressure manifold 34. For example, the installation connection structure can be made of a material that is substantially impermeable to installation fluid or can be coated with a material that is substantially impermeable to installation fluid. More specifically, the installation inlet connector 154 can be secured to the installation connection structure 150 and to the installation module 30 proximate the opening 76 to form an installation fluid flow path that is fluidly separated from the NPWT flow path.

The installation inlet connector 154 is in fluid communication with the installation connection structure 150. The installation inlet connector 154 is configured to engage the installation conduit pad 118. In the illustrated embodiment, the installation inlet connector 154 is a protrusion that extends from the connection plate 126. In some embodiments, a distal end of the installation inlet connector 154 is pointed (e.g., a spear). In some embodiments, the installation inlet connector includes a barb 162 for engaging the installation outlet connector 134 in a friction fit. Although in the illustrated embodiment the installation inlet connector 154 is shown as a protrusion and the installation outlet connector 134 is shown as a hole, in different embodiments, the installation inlet connector 154 and the installation outlet connector 134 can have different shapes as long as the installation inlet connector 154 and the installation outlet connector 134 remain capable of engagement. For example, in some embodiments, the installation inlet connector 154 can be a hole and the installation outlet connector 134 can be a protrusion.

As is best shown in FIG. 1, the NPWT inlet connector 158 is in fluid communication with the negative pressure manifold 34. In the illustrated embodiment, the NPWT inlet connector 158 is a through hole in the connection plate 126 configured to engage the NPWT outlet connector 142 in a friction fit. Although in the illustrated embodiment the NPWT inlet connector 158 is shown as a through hole and the NPWT outlet connector 142 is shown as a protrusion, in different embodiments, the NPWT inlet connector 158 and the NPWT outlet connector 142 can have different shapes as long as the NPWT inlet connector 158 and the NPWT outlet connector 142 remain capable of engagement. For example, in some embodiments, the NPWT inlet connector 158 can be a protrusion and the NPWT outlet connector 142 can be a hole.

As is apparent from FIGS. 1 and 2, the installation inlet connector 154 and the NPWT inlet connector 158 are different shapes. This is intended to prevent the installation outlet connector 134 from engaging the NPWT inlet connector 158 and to prevent the NPWT outlet connector 142 from engaging the installation inlet connector 154. As is best shown in FIG. 1, the connection plate 126 is positioned beneath the sealing member 38 and is visible through the sealing member 38. The connection plate is configured to guide an operator of the wound therapy system 10 to correctly connect the installation conduit pad 118 and the NPWT conduit pad 122. For example, the installation inlet connector 154 and the installation outlet connector 134 include a first pair of markings 166 that indicate that the installation outlet connector 134 should be connected to the installation inlet connector 154. The NPWT inlet connector 158 and the NPWT outlet connector 142 include a second pair of markings 170 that are different than the first pair of markings 166 to indicate that the NPWT outlet connector 142 should be connected to the NPWT inlet connector 158. In some embodiments, the first pair of markings 166 and the second pair of markings 170 may be colors, patterns, or shapes.

As is shown in FIG. 1, the connection plate 126 is positioned beneath the sealing member 38 when the wound dressing 14 is deployed within the patient. The installation inlet connector 154 and the installation outlet connector 134 are accessible through the sealing member 38 (e.g., by piercing the sealing member 38). The installation inlet connector 154 pierces through the sealing member 38 as the sealing member 38 is secured to the patient. The NPWT outlet connector 142 on the NPWT conduit pad 122 pierces through the sealing member 38 to connect to the NPWT inlet connector 158 of the connection plate 126. Accordingly, a first surface 174 of the connection plate 126 may be coated with an adhesive for securing the connection plate 126 to the second surface 98 of the sealing member 38 to maintain a fluid-tight seal of the abdominal cavity. The adhesive can prevent the connection plate 126 from shifting as the instillation conduit pad 118 and the NPWT conduit pad 122 are engaged with the connection plate 126. In some embodiments, the installation conduit pad 118 and the NPWT conduit pad 122 may include an adhesive layer surrounding the installation outlet connector 134 and the NPWT outlet connector 142, respectively, for forming a fluid-tight seal with the first surface of the sealing member 38. The connection plate 126 has a density that is high enough and/or a thickness that is thick enough to prevent the protrusion of the NPWT outlet connector 142 from contacting the patient and causing patient discomfort. In some embodiments, the connection plate is made of a dense open cell foam. In other embodiments, the connection plate can be made of a plastic material. In some embodiments, the connection plate 126 is made of a deformable material and/or the negative pressure manifold 34 is sized to be thicker than the connection plate 126 such that the pressure applied to the connection plate 126 as the installation conduit pad 118 and the NPWT conduit pad 122 are connected, and compression within the abdominal cavity during NPWT does not cause the connection plate 126 and/or the NPWT outlet connector 142 to cause patient discomfort.

As illustrated in FIG. 1, the wound therapy system 10 includes an installation flow path (arrows 172) that is fluidly separate from a negative pressure flow path (arrows 176). As illustrated by the arrows 172, installation fluid enters the wound therapy system 10 from the installation system 22 and travels along the installation conduit 130 to the installation conduit pad 118. The installation fluid then flows through the installation inlet connector 154 of the connection plate 126 to the installation connection structure 150. The installation fluid then enters the fluid distribution hub 72 of the installation module 30 and travels along the fluid distribution structures 74. The installation fluid exits the fluid distribution structures 74 through the fenestrations 78 and travels to the treatment site.

As illustrated by the arrows 176, the negative pressure generated by the negative pressure source 46 of the NPWT system 26 causes fluid (e.g., installation fluid, wound exudate, etc.) to enter the plurality of elongate legs 73 of the abdominal treatment device 28 through the fenestrations 77. As shown by the arrows 176, fluid travels through at least a portion of the elongate legs 73 and exits the abdominal treatment device through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Figure 3:
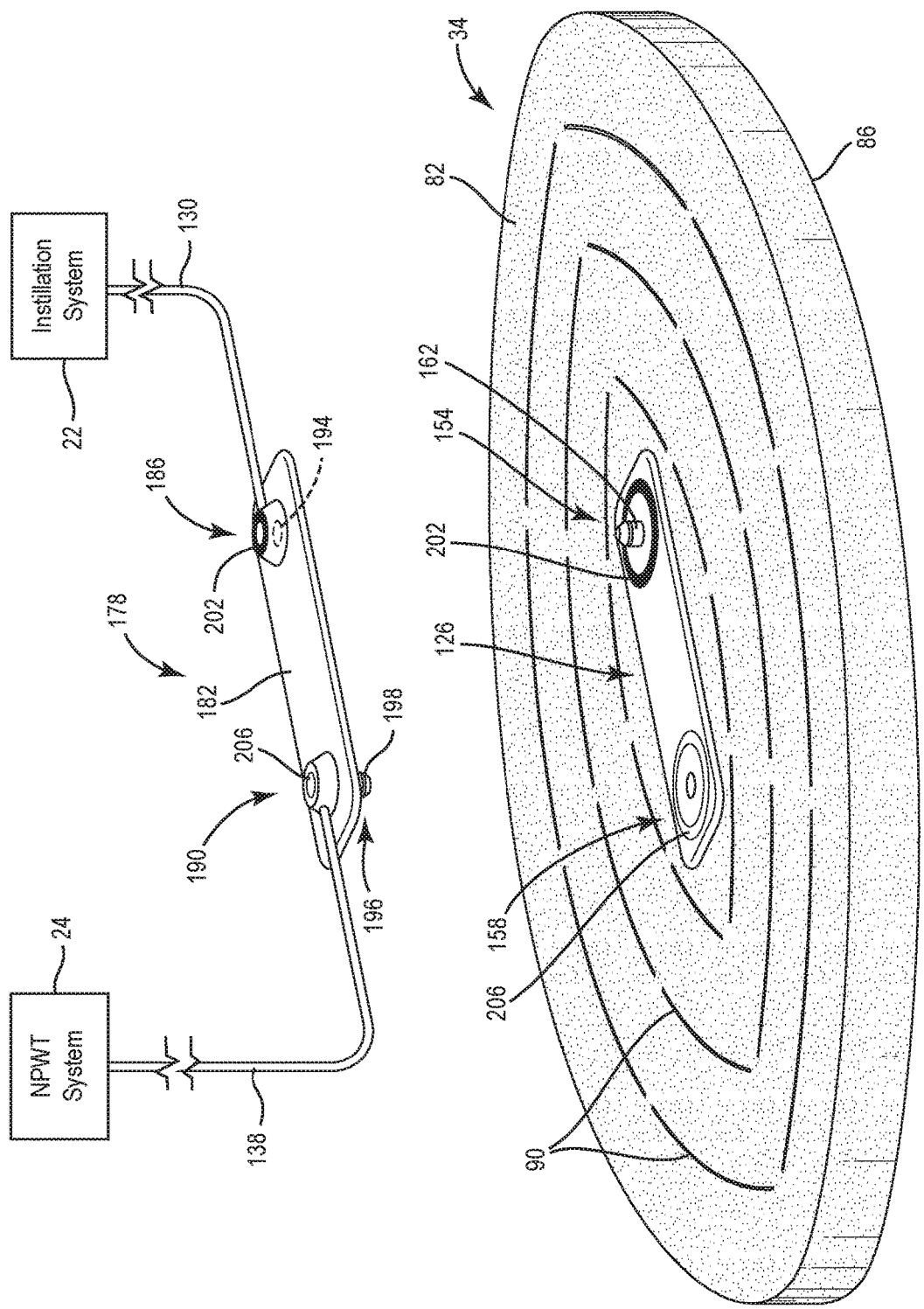
FIG. 3 is a perspective view of a connection system for use with the wound treatment system of FIG. 1 according to some embodiments.

Installation and NPWT Conduit Connection System-Integrated Installation and NPWT Pad FIG. 3 illustrates a connection system 178 for the connecting the wound therapy system 10 to the installation system 22 and the NPWT system 26, according to some embodiments. The connection system 178 is shown to include the connection plate 126 and an integrated conduit pad 182. The integrated conduit pad 182 includes an installation outlet portion 186 and a NPWT outlet portion 190. The installation outlet portion 186 is secured to the installation conduit 130 of the installation system 22 through a substantially fluid-tight connection. The installation outlet portion 186 includes an installation outlet connector 194 configured to engage the installation inlet connector 154 of the connection plate 126. In the illustrated embodiment, the installation outlet connector 194 is a hole. The NPWT outlet portion 190 is secured to the negative pressure conduit 138 of the NPWT system 26 through a substantially fluid-tight connection. The NPWT outlet portion 190 includes an NPWT outlet connector 196 configured to engage the NPWT inlet connector 158 of the connection plate 126 as described in greater detail below. In the illustrated embodiment, the NPWT outlet connector 196 is a protrusion. In some embodiments, the NPWT outlet connector 196 is a pointed protrusion (e.g., spear). In some embodiments, the NPWT outlet connector includes a barb 198. As shown in FIG. 3, in some embodiments, the installation conduit 130 and the negative pressure conduit 138 are made of low-profile and/or flexible tubing to reduce patient discomfort.

The connection plate 126 and the integrated installation and NPWT conduit pad 182 are substantially the same shape to facilitate alignment of the installation outlet connector 194 with the installation inlet connector 154 and the NPWT outlet connector 196 with the NPWT inlet connector 158. For example, the connection plate 126 is structured so that the installation inlet connector 154 and the NPWT inlet connector 158 have a fixed spacing therebetween. The integrated NPWT conduit pad 182 is structured so that the installation outlet connector 194 and the NPWT outlet connector 196 have the same fixed spacing therebetween as the spacing between the installation inlet connector 154 and the NPWT inlet connector 158. Accordingly, the integrated installation and NPWT conduit pad 182 can be configured (e.g., have a size and a spacing) to engage a connection plate 126 having specific dimensions (e.g., corresponding to a specific size and/or type of wound dressing 14).

As shown in FIG. 3, the installation inlet connector 154 and the NPWT inlet connector 158 are different shapes. This is intended to prevent the installation outlet connector 194 from engaging the NPWT inlet connector 158 and to prevent the NPWT outlet connector 196 from engaging the installation inlet connector 154. As is best shown in FIG. 3, the installation inlet connector 154 and the installation outlet connector 134 include a first pair of markings 202 that indicate that the installation outlet connector 134 should be connected to the installation inlet connector 154. The NPWT inlet connector 158 and the NPWT outlet connector 142 include a second pair of markings 206 that are different than the first pair of markings 202 to indicate that the NPWT outlet connector 142 should be connected to the NPWT inlet connector 158. In some embodiments, the first pair of markings 202 and the second pair of markings 206 may be colors, patterns, shapes, and/or words.

Compressible Installation Conduit-Bellows

Figure 4:
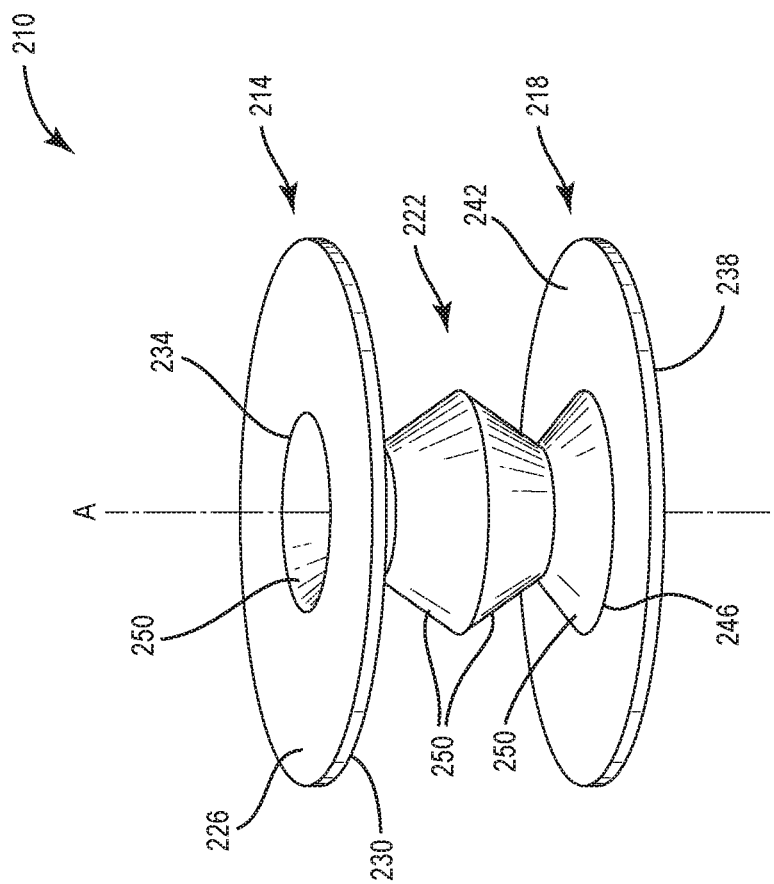
FIG. 4 is an installation fluid conduit for use with a wound treatment system according to some embodiments.

FIGS. 4-6 illustrate the negative pressure manifold 34 including a compressible installation connection structure 210. The compressible installation connection structure 210 is intended to expand and contract with the negative pressure manifold 34 as the negative pressure manifold 34 expands and contracts during cycles of NPWT therapy (e.g., the negative pressure manifold 34 and the compressible installation connection structure 210 are expanded when not under negative pressure and compressed when under negative pressure). The compressible installation connection structure 210 is also intended to expand and contract to accommodate different thicknesses of negative pressure manifold 34. As is best shown in FIG. 4, the compressible installation connection structure 210 includes a first connection plate 214, a second connection plate 218, and a flow path 222 extending between the first connection plate 214 and the second connection plate 218. The first connection plate 214 includes a first connection surface 226 and a second, negative pressure manifold-facing, surface 230. The first connection plate 214 includes a flow path inlet 234. The second connection plate 218 includes a second connection surface 238 and a first, negative pressure manifold-facing, surface 242. The second connection plate 218 includes a flow path outlet 246. As is best shown in FIG. 5, the first connection plate 214 and the second connection plate 218 are spaced apart to receive the negative pressure manifold 34 therebetween.

The flow path 222 extends between the flow path inlet 234 and the flow path outlet 246 to direct installation fluid from the installation conduit 130 of the installation system 22 to the fluid distribution hub 72 of the installation module 30. The flow path 222 defines a longitudinal axis A. The flow path 222 is flexible and is configured to expand and contract in a direction substantially defined by the longitudinal axis A. The flow path 222 is formed of a plurality of angled walls 250. The plurality of angled walls 250 are oriented to form adjacent thick and thin sections to form a bellows structure. Under negative pressure, the angled walls 250 deflect towards the horizontal, resulting in contraction in the direction defined by the longitudinal axis A. In the illustrated embodiment, the plurality of angled walls 250 includes four angled walls 250. In other embodiments, the plurality of angled walls 250 may include more or fewer angled walls. In the illustrated embodiments, plurality of angled walls 250 form conical segments. In other embodiments, the plurality of angled walls may form segments of other shapes, such as pyramidal shapes.

In some embodiments, the first connection plate 214, the second connection plate 218, and the flow path 222 are integrally formed as a single part. In other embodiments, the first connection plate 214, the second connection plate 218, and the flow path 222 may be formed separately and then secured together to form the compressible installation connection structure 210. The compressible installation connection structure 210 is made of a flexible material that is capable of withstanding cycles of expansion and contraction. The compressible installation connection structure 210 is configured to prevent lateral flow of the installation fluid into the negative pressure manifold 34. For example, the compressible installation connection structure can be made of a material that is substantially impermeable to installation fluid or can be coated with a material that is substantially impermeable to installation fluid.

FIGS. 5 and 6 illustrate the compressible installation connection structure 210 deployed in the wound therapy system 10. As shown in FIG. 5, the compressible installation connection structure 210 can be received within and extend through a hole in the negative pressure manifold 34. The second connection surface 238 of the second connection plate 218 is secured to the installation module 30 proximate the fluid distribution hub 72 such that the flow path outlet 246 is in fluid communication with the opening 76 of the fluid distribution hub 72 to generate an installation flow path that is fluidly separate from a NPWT flow path. In some embodiments, the second connection surface 238 may be welded to the installation module 30. In other embodiments, the second connection surface 238 may be secured to the installation module 30 by an adhesive. In some embodiments, such as the embodiment illustrated in FIG. 5, the first connection surface 226 of the compressible installation connection structure 210 is securable to the second surface 98 of the sealing member 38 by an adhesive. In such an embodiment, the first connection surface 226 of the compressible installation connection structure 210 can include markings (not shown) to facilitate placement of the installation conduit pad 118 (e.g., provide an indication of where to cut a hole into or pierce the sealing member 38). The compressible installation connection structure 210 can contract in response to the forces exerted by the operator when securing the installation conduit pad 118, preventing patient discomfort during placement of the installation conduit pad 118.

In other embodiments, such as the embodiment of FIG. 6, the first connection surface 226 is securable to the connection plate 42 by an adhesive. In some embodiments, the first connection surface 226 may include a marking 254 indicating that the first connection surface 226 should be secured to the connection plate 42. In some embodiments, the first connection surface 226 may include an adhesive for securing the first connection surface 226 to the connection plate 42. In such embodiments, the first connection surface may include a removable backing and the marking 254 may be positioned on the removable backing.

As illustrated in FIG. 5, the wound therapy system 10 includes an installation flow path (arrows 252) that is fluidly separate from a negative pressure flow path (arrows 256). As illustrated by the arrows 252, installation fluid enters the wound therapy system 10 from the installation system 22 and travels along the installation conduit 130 to the installation conduit pad 118. The installation fluid then flows through the installation inlet 110 of the connection plate 42 to the flow path inlet 234 of the compressible installation connection structure 210. The installation fluid travels along the flow path 222 and exits the compressible installation connection structure 210 through the flow path outlet 246. The installation fluid then enters the fluid distribution hub 72 of the installation module 30 and travels along the fluid distribution structures 74. The installation fluid exits the fluid distribution structures 74 through the fenestrations 78 and travels to the treatment site.

As illustrated by the arrows 256, the negative pressure generated by the negative pressure source 46 of the NPWT system 26 causes fluid (e.g., installation fluid, wound exudate, etc.) to enter the plurality of elongate legs 73 of the abdominal treatment device 28 through the fenestrations 77. As shown by the arrows 256, fluid travels through at least a portion of the elongate legs 73 and exits the abdominal treatment device 28 through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Installation Conduit-Compressible Foam

Figure 7:
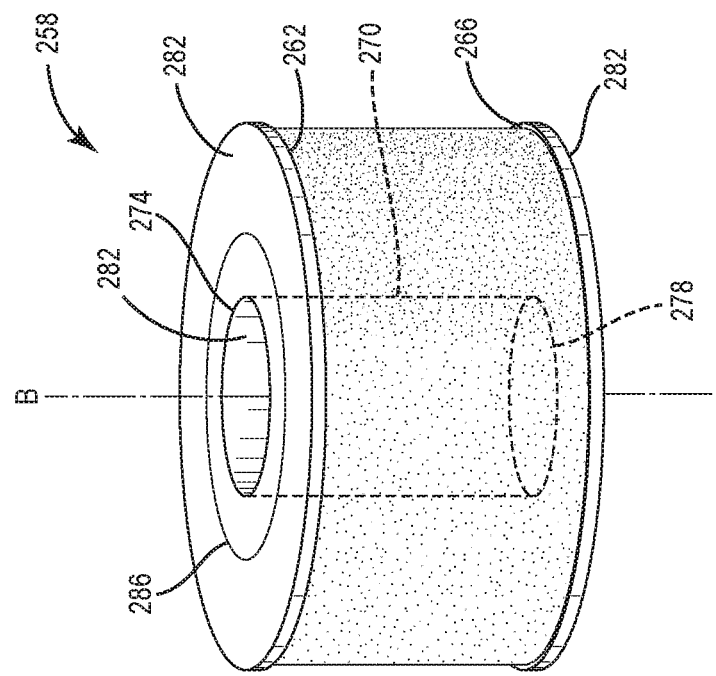
FIG. 7 is a perspective view of an installation fluid conduit for use with a wound treatment system according to some according to some embodiments.
Figure 8:
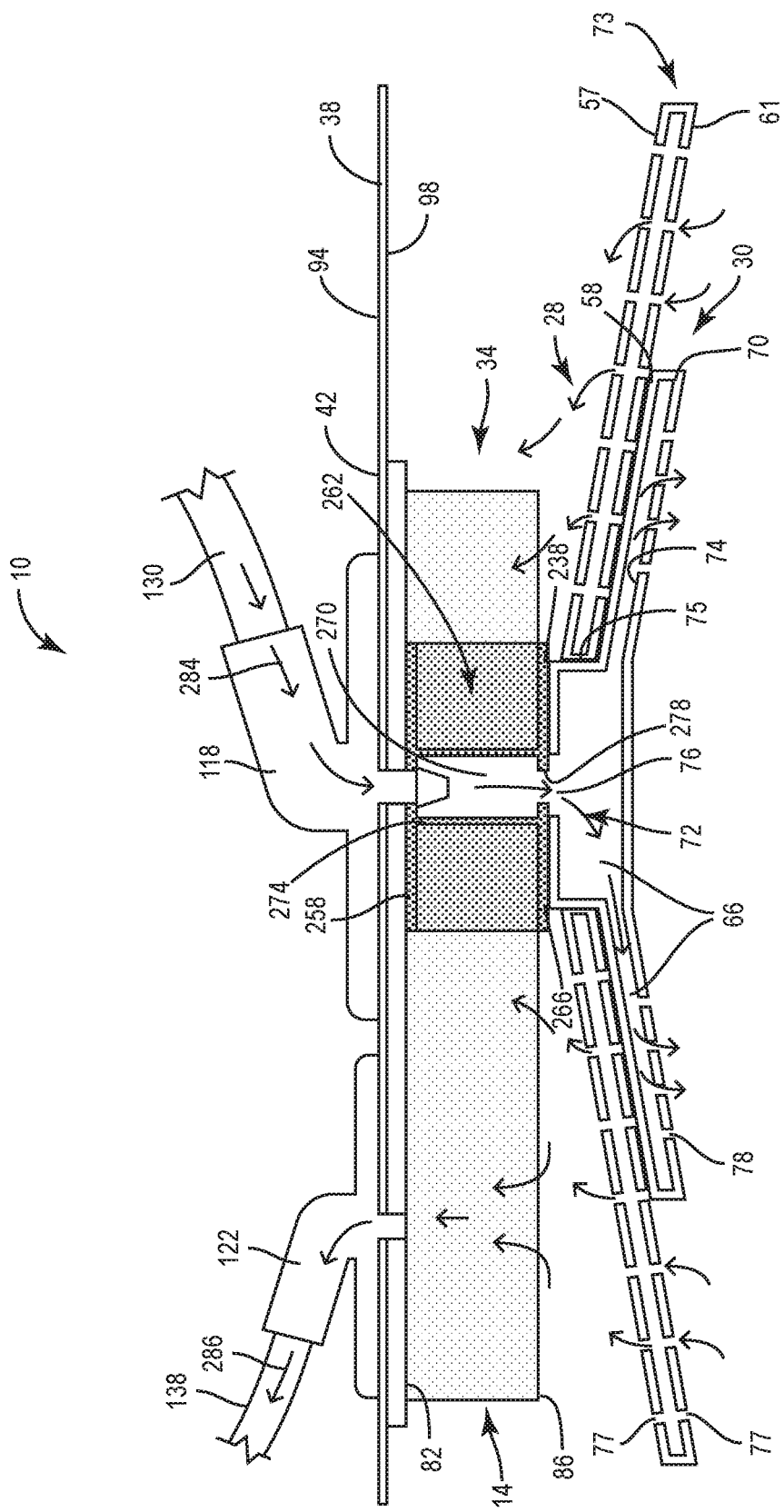
FIG. 8 is a section view of a wound treatment system including the installation fluid conduit of FIG. 7 according to some embodiments.

FIGS. 7-8 illustrate the negative pressure manifold 34 including a compressible installation connection structure 258. The compressible installation connection structure 258 is positionable within the negative pressure manifold 34 and intended to expand and contract with the negative pressure manifold 34 as the negative pressure manifold 34 expands and contracts during cycles of NPWT therapy (e.g the negative pressure manifold 34 and the compressible installation connection structure 258 are expanded when not under negative pressure and compressed when under negative pressure) to reduce patient discomfort during NPWT. The compressible installation connection structure 258 can be made of the same material as the negative pressure manifold 34 such that the compressible installation connection structure 258 compresses and expands substantially a same amount as the negative pressure manifold 34 during NPWT therapy. As is best shown in FIG. 4, the compressible installation connection structure 258 includes a first surface 262, a second, abdominal contents-facing surface 266, and a flow path 270 extending between the first surface 262 and the second surface 266.

The flow path 270 extends between a flow path inlet 274 formed in the first surface 262 and a flow path outlet 278 formed in the second surface to direct installation fluid from the installation conduit 130 of the installation system 22 to the fluid distribution hub 72 of the installation module 30. The flow path 270 defines a longitudinal axis B. A fluid impermeable layer 282 is formed on at least a portion of the first surface 262, along the flow path 270, and on at least a portion of the second surface 266 to prevent lateral flow of the installation fluid into the negative pressure manifold 34. In some embodiments, the fluid impermeable layer 282 In the illustrated embodiment, the fluid impermeable layer 282 is made of a polyurethane material. In other embodiments, the fluid impermeable layer 282 can be made of another material that is substantially impermeable to installation fluid.

The compressible installation connection structure 258 can be made of a compressive material, such that the compressible installation connection structure 258 compresses along the longitudinal axis B under negative pressure conditions. For example, the compressive installation connection structure can be made of the compressive reticulated foam material discussed above with respect to the negative pressure manifold 34. In some embodiments, the compressible installation connection structure 258 can be made of the same material as the negative pressure manifold 34 such that the compressible installation connection structure 258 compresses and expends with the negative pressure manifold 34 during cycles of NPWT.

FIG. 8 illustrates the compressible installation connection structure 258 deployed in the wound therapy system 10. The compressible installation connection structure 258 can be received within and extend through the negative pressure manifold 34. The second surface 266 is secured in a fluid-tight seal to the installation module 30 proximate the fluid distribution hub 72 such that the flow path outlet 278 is in fluid communication with the fluid distribution hub 72 to form a fluid-tight installation flow path that is fluidly separate from the NPWT flow path. In some embodiments, the second surface 266 may be welded to the installation module 30. In other embodiments, the second surface 266 may be secured to the installation module 30 by an adhesive. In some embodiments, the first surface 262 is secured with a fluid-tight seal to the connection plate 42 by an adhesive. In some embodiments, the first surface 262 is secured with a fluid-tight seal to the second surface 266 of the sealing member 38. In some embodiments, the first surface 262 may include a marking 286 indicating that the first surface 262 should be secured to the connection plate 42. In some embodiments, the first surface 262 may include an adhesive for securing the first surface 262 to the connection plate 42. In such embodiments, the first surface 262 may include a removable backing and the marking 286 may be positioned on the removable backing. In embodiments in which the second surface 266 is securable to the installation module 30 by an adhesive, second surface 266 may include a marking (not shown) indicating that the second surface 266 should be secured to the installation module 30. In some embodiments, the second surface 266 may include an adhesive for securing the second surface 266 to the installation module 30. In such embodiments, the second surface 266 may include a removable backing and the marking 286 may be positioned on the removable backing. In some embodiments, the marking 286 may be a color, a pattern, shapes, and/or words.

As illustrated in FIG. 8, the wound therapy system 10 includes an installation flow path (arrows 284) that is fluidly separate from a negative pressure flow path (arrows 286). As illustrated by the arrows 284, installation fluid enters the wound therapy system 10 from the installation system 22 and travels along the installation conduit 130 to the installation conduit pad 118. The installation fluid then flows through the installation inlet 110 of the connection plate 42 to the flow path inlet 274 of the compressible installation connection structure 258. The installation fluid travels along the flow path 270 and exits the compressible installation connection structure 258 through the flow path outlet 278. The installation fluid then enters the fluid distribution hub 72 of the installation module 30 and travels along the fluid distribution structures 74. The installation fluid exits the fluid distribution structures 74 through the fenestrations 78 and travels to the treatment site.

As illustrated by the arrows 286, the negative pressure generated by the negative pressure source 46 of the NPWT system 26 causes fluid (e.g., installation fluid, wound exudate, etc.) to enter the plurality of elongate legs 73 of the abdominal treatment device 28 through the fenestrations 77. As shown by the arrows 286, fluid travels through at least a portion of the elongate legs 73 and exits the abdominal treatment device through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Integrated Installation Conduit

Figure 9:
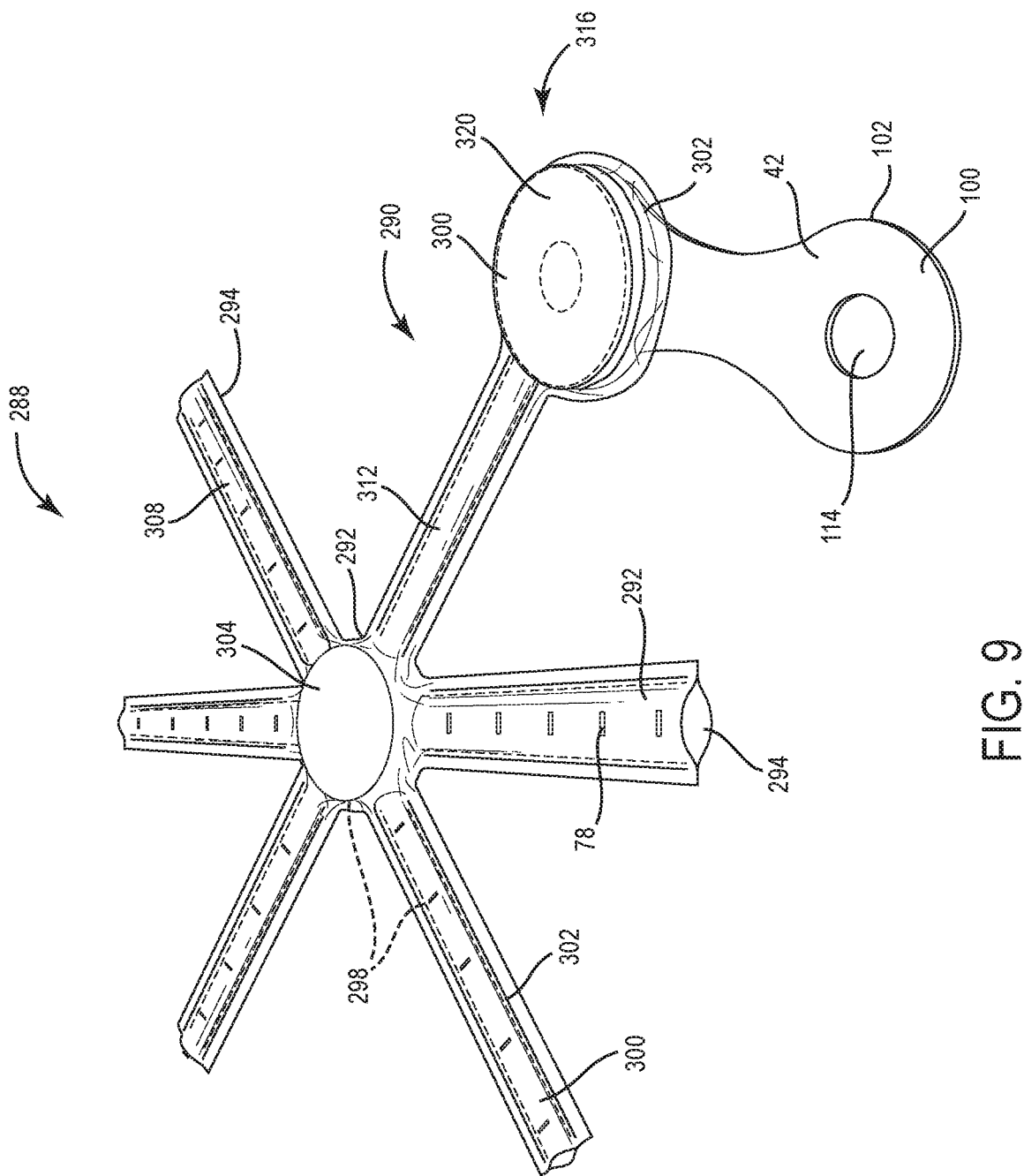
FIG. 9 is a perspective view of an installation module having an integrated installation fluid connection interface according to some embodiments.
Figure 10:
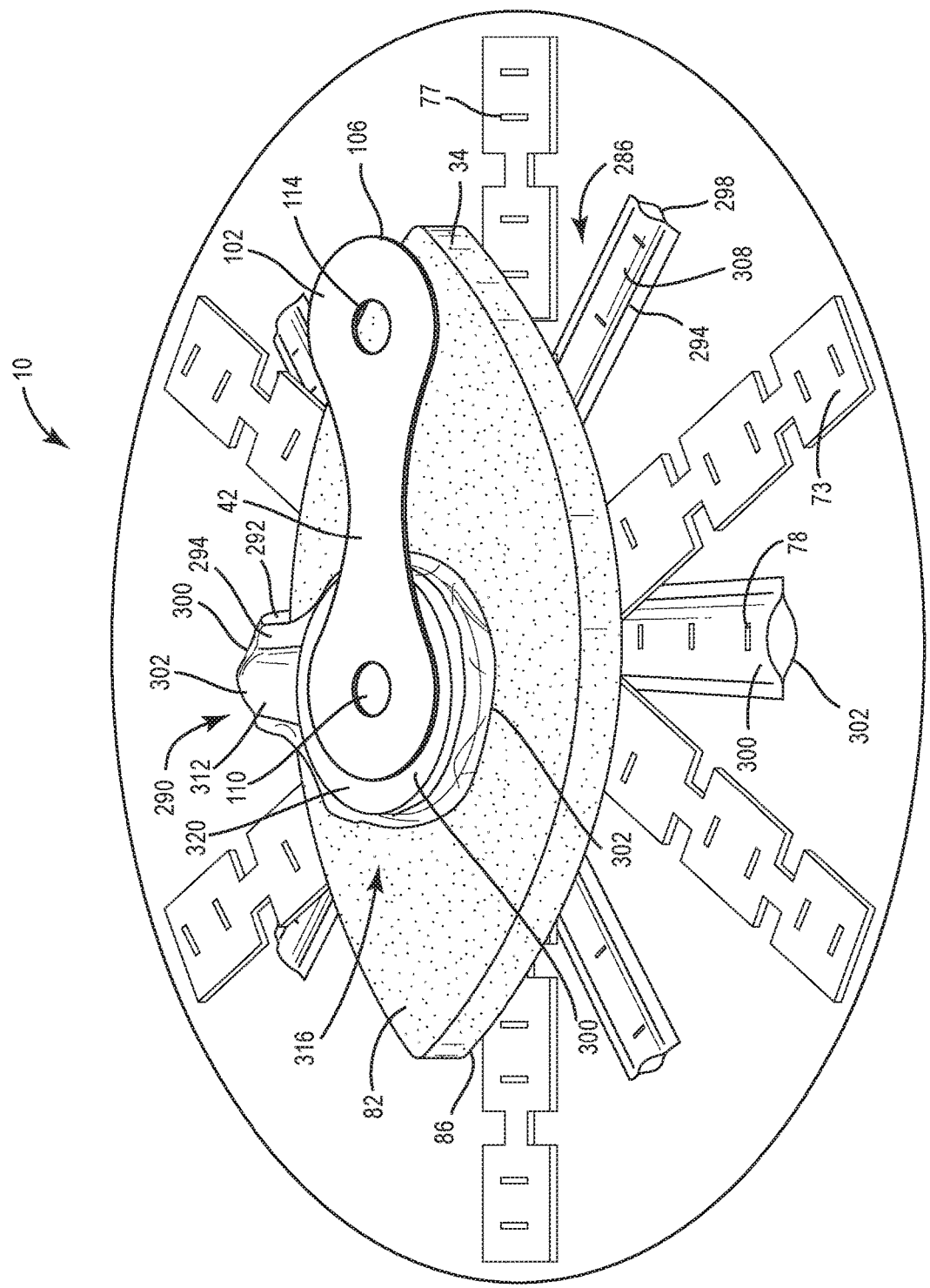
FIG. 10 is a perspective view of a wound treatment system including the installation module of FIG. 9 according to some embodiments.

FIGS. 9-10 illustrate an installation module 288 including an integrated installation conduit 290 according to some embodiments. The installation module 288 is configured to facilitate substantially even distribution of the installation fluid independently of a position of the patient (e.g., supine or lying on a side). The installation module 288 includes a first layer 292, a second layer 294, and a fluid distribution layer 298. The fluid distribution layer 298 includes a first surface 300 and a second, abdominal contents-facing, surface 302. The fluid distribution layer 298 includes a fluid distribution hub 304, a plurality of fluid distribution structures 308 that extend radially from the fluid distribution hub 304, and the integrated installation conduit 290 that extends from the fluid distribution hub 304. The first layer 292, the second layer 294, the fluid distribution hub 304, and the plurality of fluid distribution structures 308 are substantially similar to the first layer 58, the second layer 62, the fluid distribution hub 72, and the plurality of fluid distribution structures 74 described above with respect to the installation module 30 and will not be described in detail herein for the sake of brevity.

The installation conduit 290 includes a generally elongate portion 312 that extends from the fluid distribution hub 304. A distal end 316 of the generally elongate portion 312 may be enlarged to form an installation conduit land portion 320. The installation conduit land portion 320 is configured to engage the connection plate 42 and/or form a surface for engagement with the installation conduit 290. A portion of the first layer 292 and the second layer 294 encapsulates the installation conduit (e.g., the generally elongate portion 312 and the installation conduit land portion 320). The portion is made of a fluid-impermeable material and does not include the fenestrations 78 such that installation fluid may enter the installation conduit 290 at the installation conduit land portion 320 and/or the distal end 316 and travel along the elongate portion 312 to the fluid distribution hub 304 for distribution to fluid distribution structures 308.

FIG. 10 illustrates the installation module 288 and the negative pressure manifold 34 positioned to treat an open abdomen of a patient. In the illustrated embodiment, the elongate portion 312 of the installation conduit 290 is wrapped around the negative pressure manifold 34 such that the first layer 292 and the first surface 300 of the elongate portion 312 abuts the negative pressure manifold 34. In some embodiments, the portion of the first layer 292 abutting the negative pressure manifold 34 may include an adhesive for securing the first layer 292 to the negative pressure manifold 34 to prevent the installation conduit 290 from slipping. The second layer 294 of the integrated installation conduit 290 (e.g., the second surface 302 of the installation conduit land portion 320) faces away from the first surface 82 of the negative pressure manifold 34. In some embodiments, at least a portion of the second layer 294 includes an adhesive for securing the second layer 294 to the second surface 98 of the sealing member 38. In the illustrated embodiment, the connection plate 42 is secured to the installation conduit land portion 320, for example by welding and/or an adhesive. In other embodiments, the elongate portion 312 of the installation conduit may extend through a hole in the negative pressure manifold 34. Accordingly, the installation conduit 290 forms a flow path between the installation conduit 290 engaged with the installation system 22 and the fluid distribution hub 304 in a fluidly separated flow path from the flow path between the negative pressure manifold 34 and the NPWT system 26.

The wound therapy system 10 includes an installation flow path that is fluidly separate from a negative pressure flow path. The installation fluid enters the wound therapy system 10 from the installation system 22 and travels along the installation conduit 130 to the installation conduit pad 118. The installation fluid then flows through the installation inlet 110 of the connection plate 42 to the installation conduit land portion 320 of the installation conduit 290 of the installation module 30. The installation fluid travels along the generally elongate portion 312 of the installation conduit 290 and then enters the fluid distribution hub 72. The installation fluid then enters and travels along the fluid distribution structures 74. The installation fluid exits the fluid distribution structures 74 through the fenestrations 78 and travels to the treatment site.

The negative pressure generated by the negative pressure source 46 of the NPWT system 26 causes fluid (e.g., installation fluid, wound exudate, etc.) to enter the plurality of elongate legs 73 of the abdominal treatment device 28 through the fenestrations 77. Fluid travels through at least a portion of the elongate legs 73 and exits the abdominal treatment device through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Integrated Installation Conduit

Figure 11:
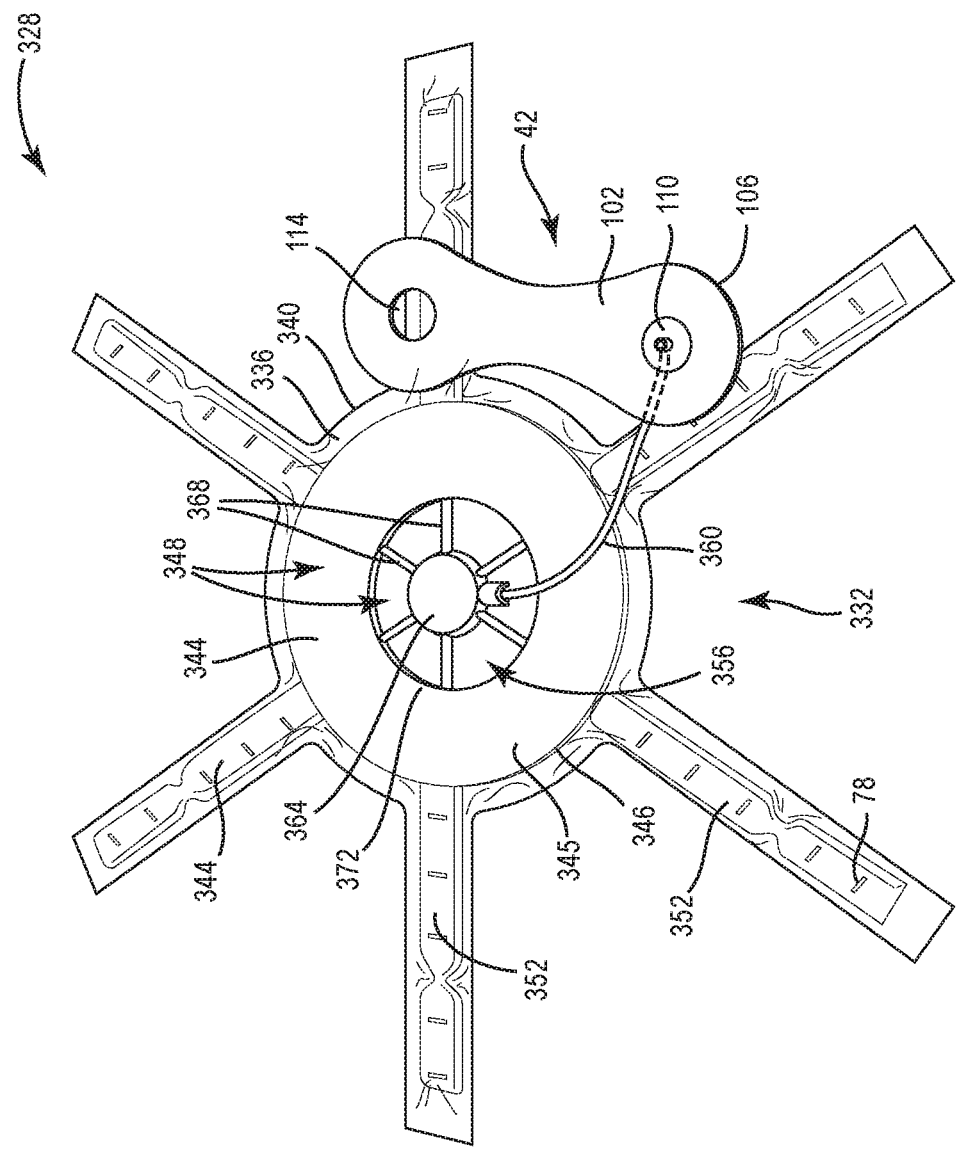
FIG. 11 is a perspective view of an installation module having an integrated installation fluid connection interface according to some embodiments.

FIGS. 11-12 illustrate an installation module 328 including an integrated installation conduit 332 according to some embodiments. The installation module includes 328 a first layer 336, a second layer 340, and a fluid distribution layer 344. The fluid distribution layer 344 includes a first layer 345 and a second, abdominal contents-facing, later 346. The fluid distribution layer 344 includes a fluid distribution hub 348 and a plurality of fluid distribution structures 352 that extend radially from the fluid distribution hub 348, and the installation conduit 332 that extends from the fluid distribution hub 348. The first layer 336, the second layer 340, and the plurality of fluid distribution structures 352 are substantially similar to the first layer 58, the second layer 62, and the plurality of fluid distribution structures 74 described above with respect to the installation module 30 and will not be described in detail herein for the sake of brevity.

The installation conduit 332 includes a fluid distribution hub engagement portion 356 and flow path portion 360. The flow path portion 360 is engaged with the fluid distribution hub engagement portion 356 and the connection plate 42. In the illustrated embodiment, the flow path portion 360 is flexible tubing. The flow path portion 360 is configured to enable motion of the installation module 328 and the negative pressure manifold 34 during cycles of NPWT. More specifically, the ends of the flow path portion 360 are in-molded into the fluid distribution hub engagement portion 356 and the connection plate 42. The fluid distribution hub engagement portion 356 includes installation fluid inlet portion 364 engaged with the flow path portion 360 and a plurality of channels 368 in fluid communication with each of the fluid distribution structures of the plurality of fluid distribution structures 352. In the illustrated embodiment, the plurality of channels 368 are molded into the fluid distribution hub engagement portion 356.

The fluid distribution hub 348 includes a hole 372 sized to receive the fluid distribution hub engagement portion 356. The fluid distribution hub engagement portion 356 is secured within the hole 372. In some embodiments, the first layer 336 and the second layer 340 may extend over (e.g., encapsulate) the fluid distribution hub engagement portion 356. In other embodiments, the first layer 336 and the second layer 340 encapsulate the fluid distribution layer 344, including the walls of the hole 372. In such an embodiment, the fluid distribution hub engagement portion 356 may be welded to the first layer 336 and the second layer 340, and the first layer 336 and the second layer 340 may include fenestrations aligned with the plurality of channels 368 to allow installation fluid to enter the fluid distribution hub 348.

FIG. 12 illustrates the installation module 328 and the negative pressure manifold 34 positioned to treat an open abdomen of a patient. The flow path portion 360 of the installation conduit 332 is wrapped around the negative pressure manifold 32 such that the flow path portion 360 and the connection plate 42 overlie the first surface 82 of the negative pressure manifold 34. The connection plate 42 may be secured to the first surface of the negative pressure manifold 34, for example by welding and/or an adhesive. Accordingly, the installation conduit 332 forms a flow path between the installation conduit 332 engaged with the installation system 22 and the fluid distribution hub 348 in a fluidly separated flow path. As illustrated in FIG. 12 in some embodiments, a second installation module can be used.

The wound therapy system 10 includes an installation flow path that is fluidly separate from a negative pressure flow path. The installation fluid enters the wound therapy system 10 from the installation system 22 and travels along the installation conduit 130 to the installation conduit pad 118. The installation fluid then flows through the installation inlet 110 of the connection plate 42 to the flow path portion 360 of the installation conduit 332. The installation fluid travels along flow path portion 360 of the installation conduit 332 and then enters the fluid distribution hub 72. The installation fluid then enters and flows along the plurality of channels 368 to the plurality of fluid distribution structures 352. The installation fluid exits the fluid distribution structures 352 through the fenestrations 78 and travels to the treatment site.

The negative pressure generated by the negative pressure source 46 of the NPWT system 26 causes fluid (e.g., instillation fluid, wound exudate, etc.) to enter the plurality of elongate legs 73 of the abdominal treatment device 28 through the fenestrations 77. Fluid travels through at least a portion of the elongate legs 73 and exits the abdominal treatment device through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Integrated Instillation Conduit With Friction Fit Seal

Figure 13:
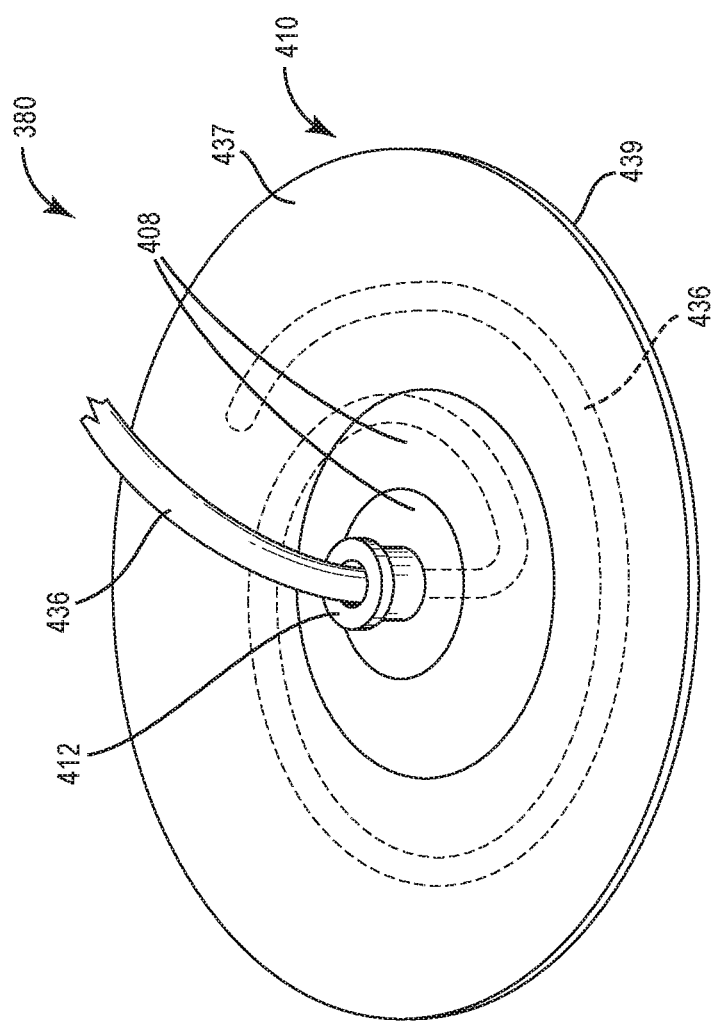
FIG. 13 is a perspective view of an installation connection sealing system for a wound treatment system according to some embodiments.
Figure 14:
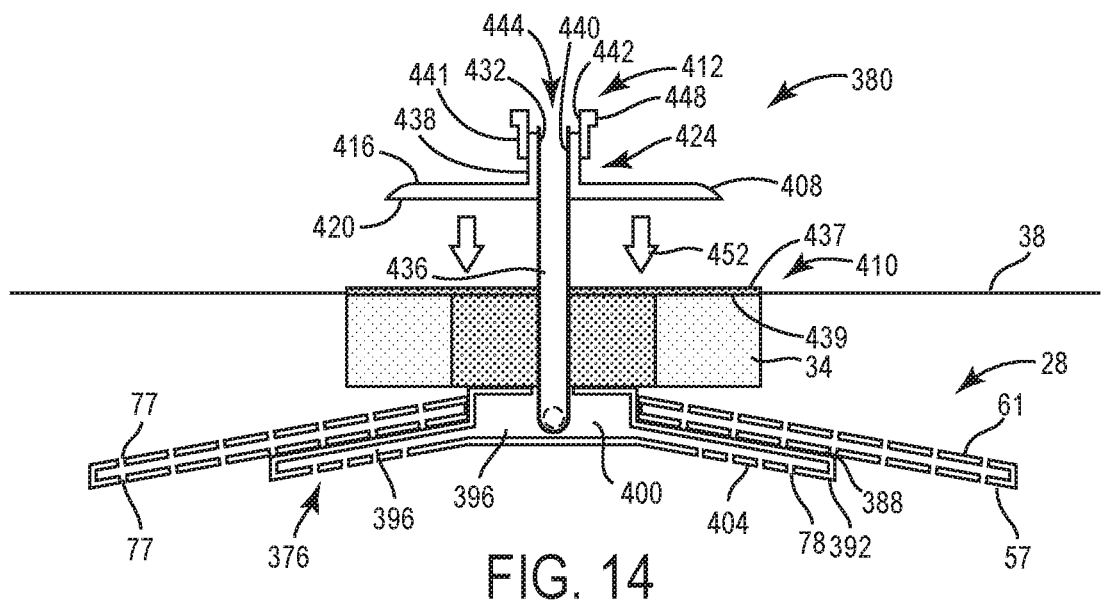
FIGS. 14-16 illustrate a process of securing the installation connection sealing system to generate a fluid-tight seal.
Figure 15:
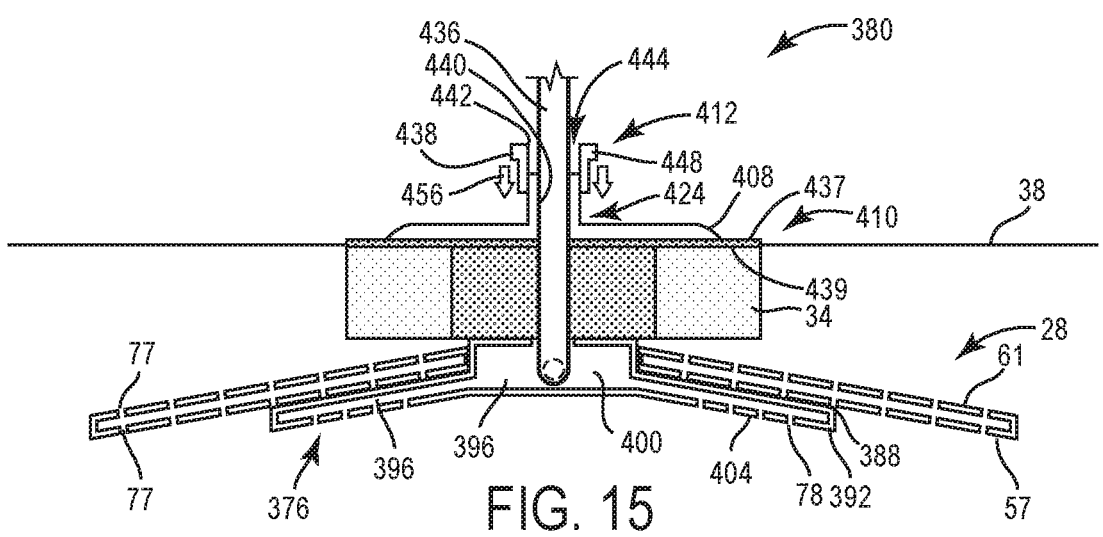
Figure 16:
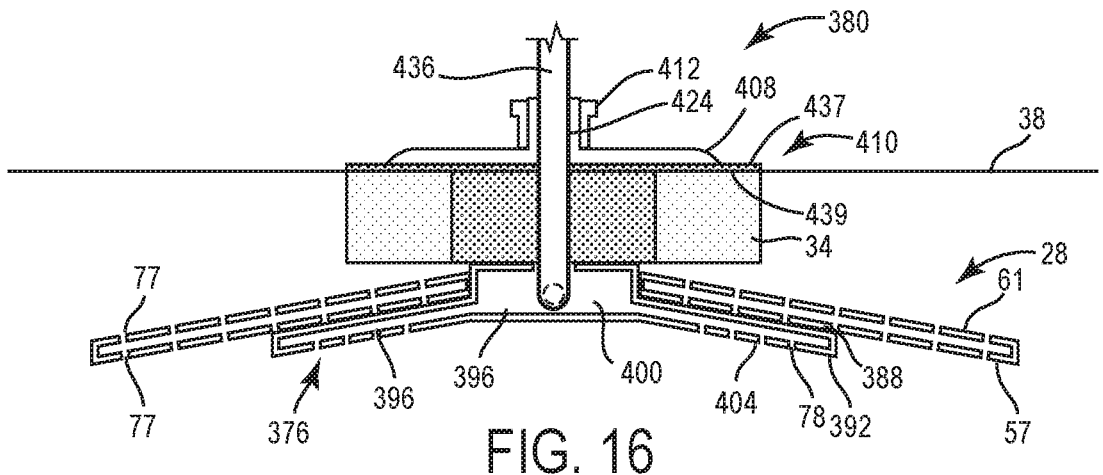

FIGS. 13-17 illustrate an instillation module 376 and an instillation connection sealing system 380. The instillation module 376 and the instillation connection sealing system 380 can be used in conjunction with the abdominal treatment device 28. FIG. 13 illustrates a top perspective view of the instillation module 376 and the instillation connection sealing system 380 in a storage position. FIGS. 14-16 illustrate steps in a process for deploying the instillation module 376 and the instillation connection sealing system 380.

As is best shown in FIGS. 14-17, the instillation module 376 including an integrated instillation conduit 436, a first layer 388, a second layer 392, and a fluid distribution layer 396. The fluid distribution layer 396 includes a fluid distribution hub 400, and a plurality of fluid distribution structures 404 that extend radially from the fluid distribution hub 400. The first layer 388, the second layer 392, the fluid distribution hub 400, and the plurality of fluid distribution structures 404 are substantially similar to the first layer 58, the second layer 62, the fluid distribution hub 72, and the plurality of fluid distribution structures 74 described above with respect to the instillation module 30 and will not be described in detail herein for the sake of brevity. The integrated instillation conduit 436 is in fluid communication with the fluid distribution hub 400 and is secured to the instillation module 376 using a fluid-tight connection. In some embodiments, the integrated instillation conduit 436 may be secured to the instillation module 376 using the fluid distribution hub engagement portion 356 described above with respect to FIGS. 11-12. In the illustrated embodiment, the integrated instillation conduit 436 is a flexible tube. In some embodiments, the integrated instillation conduit 436 may be provided in a storage position in which the integrated instillation conduit 436 is provided in a coil abutting the instillation module 376. Once positioned in the abdominal cavity, the integrated instillation conduit 436 can be uncoiled and deployed in the patient as described in greater detail below.

The instillation connection sealing system 380 includes a sealing plate 408, a sealing pad 410 and a locking collar 412. The sealing plate 408 includes a first surface 416 and a second, wound-facing surface 420. The sealing plate 408 further includes an instillation conduit passage 424 that extends between the first surface 416 and the second surface 420. A portion of the instillation conduit passage 424 extends above the first surface 416. The instillation conduit passage 424 includes an exterior surface 438 and an interior surface 440 that defines a passageway for receiving the instillation conduit 436. At least a portion of the second surface 420 includes an adhesive for securing the second surface 420 of the sealing plate 408 to the first surface 416 of the sealing member 38 in a fluid-tight seal.

The sealing pad 410 includes a first surface 437 and a second, wound-facing, surface 439. The second surface 439 includes an adhesive coating. The sealing pad 410 is sized to form a seal around a hole formed in the sealing member 38 to retrieve the instillation conduit 436 as described in greater detail below. In some embodiments, the sealing pad 410 can be made from the same material as the sealing member 38.

The locking collar 412 includes an exterior surface 441 and an interior surface 442 that define a passageway 444. The passageway 444 is sized such that the locking collar 412 can move freely along the instillation conduit 436. The passageway 444 is sized to form a tight, friction fit against the exterior surface 440 of the instillation conduit passageway 444 of the sealing plate 408 to form a fluid-tight seal about a perimeter of the instillation conduit 436. In some embodiments, the locking collar 412 is more rigid than the instillation conduit passageway 424 and is sized such that engagement of the locking collar 412 with the instillation conduit passageway 424 causes the instillation conduit passageway 424 to deform inwards against the instillation conduit 436, forming a tight seal about the perimeter of the instillation conduit 436. In some embodiments, the locking collar 412 further includes a flange 448 formed about a portion of the exterior surface 441 of the locking collar 412 to assist an operator in grasping the locking collar 412.

FIGS. 14-16 illustrate a process for deploying the instillation module 376 and the instillation connection sealing system 380. As shown in FIG. 14, the operator positions the instillation module 376 against the abdominal contents of the patient. The operator then uncoils the instillation conduit 436 from the storage position (FIG. 13) and extends the instillation conduit 436 through a hole in the negative pressure manifold 34 or wraps the instillation conduit 436 around a side of the negative pressure manifold 34. The operator then secures the sealing member 38 to the skin of the patient surrounding the abdominal incision. The operator then makes a hole in the sealing member 38 and passes the instillation conduit 436 through the hole in the sealing member 38. The user then positions the sealing pad 405, the sealing plate 408 and the locking collar 412 along the instillation conduit 436 such that the second surface 98 of the sealing member 38 is oriented toward the first surface 416 of the sealing member 38. The user then slides the sealing pad 410 towards the sealing member 38 and secures the second surface 407 of the sealing pad 410 around the hole in the sealing member 38. The user then slides the sealing plate 408 and the locking collar towards the sealing member 38 as indicated by the arrows 452. The user secures the second surface 420 of the sealing plate 408 to the first surface 437 of the sealing pad 410 in a fluid-tight seal. As shown in FIG. 15, the user then slides the locking collar 412 towards the first surface 416 of the sealing plate, as shown by the arrows 456, to engage the locking collar 412 in a friction-fit and establish a fluid-tight seal between the instillation conduit passage 424 and the instillation conduit 436, as shown in FIG. 16. The operator may then connect the installation conduit 436 to the installation system 22 and begin installation therapy.

Figure 17:
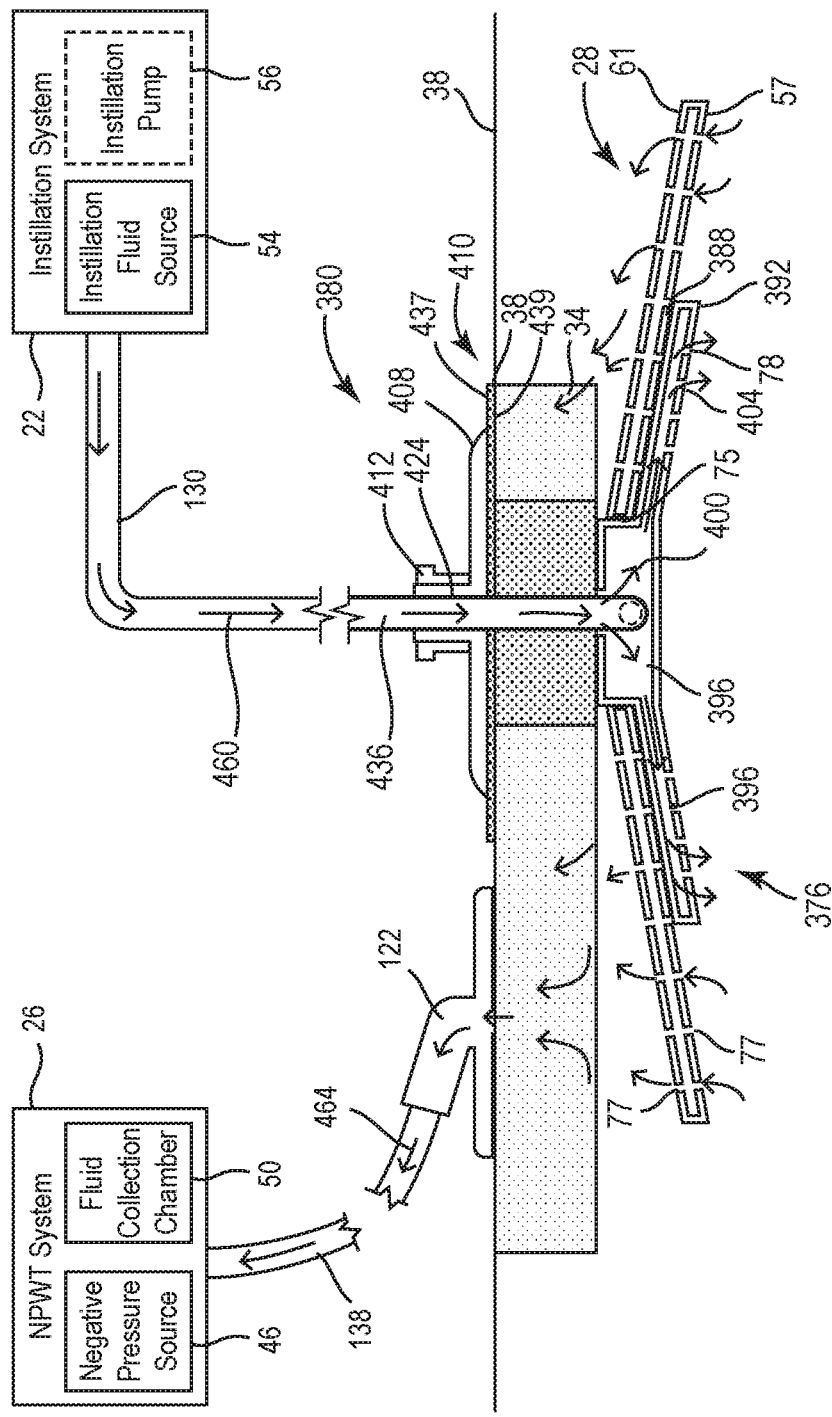
FIG. 17 illustrates a perspective view of the wound treatment system including the installation connection sealing system.

FIG. 17 illustrates a perspective view of the wound therapy system 10 including the instillation module 376 and instillation connection sealing system 380 engaged with the instillation system 22 for providing instillation therapy and the negative pressure manifold 34 engaged with the NPWT system 26 for providing NPWT. As illustrated in FIG. 17, when the wound therapy system 10 is deployed in the patient, the wound therapy system includes an instillation flow path (arrows 460) that is fluidly separate from a negative pressure flow path (arrows 464). As illustrated by the arrows 460, instillation fluid enters the wound therapy system 10 from the instillation system 22 and travels along the instillation conduit 130 to the fluid distribution hub 400 of the installation module 376. The instillation fluid then flows along the fluid distribution structures 404. The instillation fluid exits the fluid distribution structures 404 through the fenestrations 78 and travels to the treatment site.

As illustrated by the arrows 464, the negative pressure generated by the negative pressure source 46 of the NPWT system 26 causes fluid (e.g., instillation fluid, wound exudate, etc.) to enter the plurality of elongate legs 73 of the abdominal treatment device 28 through the fenestrations 77. As shown by the arrows 176, fluid travels through at least a portion of the elongate legs 73 and exits the abdominal treatment device through the fenestrations 77. The fluid then travels through the negative pressure manifold 34 to the NPWT inlet connector 158 of the connection plate 126. The fluid then travels along the NPWT conduit pad 122 to the negative pressure conduit 138 and into the fluid collection chamber 50 of the NPWT system 26.

Combination of Components

Although the systems and methods disclosed herein are described in the context of the various embodiments illustrated herein, it is contemplated that any of the systems and methods disclosed herein can be combined in different manners.

CONFIGURATION OF EXEMPLARY EMBODIMENTS

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A system for providing instillation fluid to a deep abdominal wound, the system comprising:
    an instillation module defining a first surface and a second, abdominal contents-facing surface, the instillation module including a distribution hub configured to receive instillation fluid from an instillation fluid source;
    a connection structure comprising:
        a first surface;
        a second, abdominal contents-facing surface; and
        a flow path extending between the first surface of the connection structure and the second surface of the connection structure, the flow path including an inlet configured to receive an instillation fluid conduit engaged with the instillation fluid source and an outlet in fluid communication with the instillation module, the flow path defining an axis extending between the inlet and the outlet and configured to compress in a direction defined by the axis; and
    a negative pressure manifold defining a first surface and a second, abdominal contents-facing surface, the second surface of the negative pressure manifold directly coupled to the first surface of the instillation module, and wherein the flow path extends through the negative pressure manifold such that the flow path is positioned within the negative pressure manifold.

2. The system of claim 1, wherein at least a portion of the flow path is articulated to facilitate compression.

3. The system of claim 1, wherein at least the flow path is configured to compress under negative pressure provided by a negative pressure source.

4. The system of claim 1, wherein the second surface of the connection structure is secured to the first surface of the instillation module to provide a fluid-tight connection between the flow path and the instillation module.

5. The system of claim 1, wherein the negative pressure manifold is formed of a compressible material and the connection structure is formed of the compressible material such that the negative pressure manifold and the connection structure collapse by substantially a same amount under negative pressure.

6. The system of claim 1, further comprising a first connection plate including the first surface of the connection structure, a second connection plate including the second surface of the connection structure, and wherein the first connection plate, the second connection plate, and the flow path are integrally formed.

7. The system of claim 1, further comprising a connection plate positioned adjacent the first surface of the connection structure, the connection plate including indicia for accurately positioning the instillation fluid conduit.

8. The system of claim 1, wherein the first surface of the connection structure includes a first fluid-impermeable coating, the second surface of the connection structure includes a second fluid-impermeable coating, and the flow path includes a flow path fluid-impermeable coating.

9. The system of claim 1, wherein the instillation module and the connection structure are positionable within an incision of the deep abdominal wound.

* * * * *